(12) United States Patent (10) Patent No.: US 7,942,814 B2
Remijan et al. (45) Date of Patent: May 17, 2011

(54) MINIATURE ENDOSCOPE WITH IMAGING FIBER SYSTEM

(75) Inventors: Paul Remijan, Holland, MA (US); James E. McDonald, Monson, MA (US)

(73) Assignee: Visionscope Technologies LLC, Portsmouth, NH (US)

( * ) Notice: Subject to any disclaimer, the term of this patent is extended or adjusted under 35 U.S.C. 154(b) by 896 days.

(21) Appl. No.: 11/072,685

(22) Filed: Mar. 4, 2005

(65) Prior Publication Data

US 2006/0015014 A1 Jan. 19, 2006

Related U.S. Application Data

(63) Continuation of application No. 10/042,126, filed on Oct. 19, 2001, now Pat. No. 6,863,651.

(51) Int. Cl.
*A61B 1/00* (2006.01)
*A61B 1/04* (2006.01)
*A61B 1/06* (2006.01)

(52) U.S. Cl. .................. 600/121; 600/138; 600/182

(58) Field of Classification Search .................. 600/112, 600/114, 121–125, 182
See application file for complete search history.

(56) References Cited

U.S. PATENT DOCUMENTS

| | | | |
|---|---|---|---|
| 3,261,349 A | 7/1966 | Wallace | |
| 3,902,880 A | 9/1975 | Strack | |
| 3,941,121 A | 3/1976 | Olinger et al. | |
| 4,254,762 A | 3/1981 | Yoon | |
| 4,593,937 A | 6/1986 | Yoshida et al. | |
| 4,593,973 A | 6/1986 | Yoshida et al. | |
| 4,607,622 A | 8/1986 | Fritch et al. | |
| 4,641,912 A | 2/1987 | Goldenberg | |
| 4,790,295 A * | 12/1988 | Tashiro | 600/176 |
| 4,802,461 A | 2/1989 | Cho | 128/7 |
| 4,854,302 A | 8/1989 | Allred, III | 128/6 |
| 4,878,485 A | 11/1989 | Adair | |
| 4,904,246 A | 2/1990 | Atkinson | |
| 4,921,326 A | 5/1990 | Wild et al. | 350/96.26 |
| 4,947,245 A | 8/1990 | Ogawa et al. | |
| 5,074,642 A | 12/1991 | Hicks | |
| 5,121,740 A | 6/1992 | Uram | 128/6 |

(Continued)

FOREIGN PATENT DOCUMENTS

DE 88 14 573.5 1/1990

(Continued)

OTHER PUBLICATIONS

Rol, P., et al. "Optical Properties of Minituarized Endoscopes for Ophthalmic Use", *Optical Engineering*, vol. 34, No. 7, pp. 2070-2077.

*Primary Examiner* — Philip R Smith
(74) *Attorney, Agent, or Firm* — Weingarten, Schurgin, Gagnebin & Lebovici LLP

(57) ABSTRACT

An endoscope has a fiber optic waveguide that transmits an image from a distal end to a proximal end, the waveguide having an outer diameter of less than 3 mm. A lens system is positioned at the distal end of the fiber optic waveguide. An imaging device is optically coupled to the proximal end of fiber optic waveguide. A disposable sheath extends about the fiber optic waveguide to provide a sterile barrier, and in a preferred embodiment the sheath includes an illumination channel. In a preferred embodiment, the lens system has a first lens element, a second lens element and an aperture stop.

62 Claims, 20 Drawing Sheets

U.S. PATENT DOCUMENTS

| | | | |
|---|---|---|---|
| 5,156,142 A | 10/1992 | Anapliotis et al. | |
| 5,159,919 A | 11/1992 | Chikama | |
| 5,168,863 A | 12/1992 | Kurtzer | |
| 5,172,685 A | 12/1992 | Nudelman | 128/6 |
| 5,184,602 A | 2/1993 | Anapliotis et al. | |
| 5,237,984 A | 8/1993 | Williams, III et al. | |
| 5,274,500 A | 12/1993 | Dunn | |
| 5,290,279 A | 3/1994 | Bonati et al. | |
| 5,323,766 A | 6/1994 | Uram | |
| 5,337,734 A | 8/1994 | Saab | |
| 5,341,240 A | 8/1994 | Broome | |
| 5,347,990 A | 9/1994 | Ebling et al. | |
| 5,369,525 A | 11/1994 | Bala et al. | |
| 5,402,768 A | 4/1995 | Adair | |
| 5,406,938 A | 4/1995 | Mersch et al. | |
| 5,413,092 A | 5/1995 | Williams, III et al. | |
| 5,458,132 A | 10/1995 | Yabe et al. | |
| 5,476,090 A | 12/1995 | Kishi | |
| 5,483,951 A | 1/1996 | Frassica et al. | |
| 5,496,259 A | 3/1996 | Perkins | |
| 5,538,497 A | 7/1996 | Hori | |
| 5,569,161 A | 10/1996 | Ebling et al. | |
| 5,573,493 A | 11/1996 | Sauer et al. | |
| 5,573,496 A | 11/1996 | Sauer et al. | |
| 5,575,757 A * | 11/1996 | Kennedy et al. | 600/167 |
| 5,582,190 A * | 12/1996 | Slavin et al. | 128/898 |
| 5,591,160 A | 1/1997 | Reynard | |
| 5,591,192 A | 1/1997 | Privitera et al. | |
| 5,599,278 A | 2/1997 | Hibbard | 600/133 |
| 5,617,498 A | 4/1997 | Cawood | |
| 5,630,784 A | 5/1997 | Siegmund et al. | |
| 5,630,788 A | 5/1997 | Forkner et al. | 600/182 |
| 5,685,822 A | 11/1997 | Harhen | |
| 5,690,605 A | 11/1997 | Hamlin et al. | |
| 5,702,348 A | 12/1997 | Harhen | |
| 5,704,892 A | 1/1998 | Adair | |
| 5,751,341 A | 5/1998 | Chaleki et al. | 348/65 |
| 5,788,628 A | 8/1998 | Matsuno et al. | |
| 5,817,015 A | 10/1998 | Adair | |
| 5,827,177 A | 10/1998 | Oneda et al. | |
| 5,873,814 A * | 2/1999 | Adair | 600/109 |
| 5,876,329 A | 3/1999 | Harhen | |
| 5,879,287 A | 3/1999 | Yoshihashi | |
| 5,879,289 A | 3/1999 | Yarush et al. | |
| 5,882,295 A | 3/1999 | Kope | |
| 5,892,630 A | 4/1999 | Broome | |
| 5,919,130 A | 7/1999 | Monroe et al. | |
| 5,928,137 A * | 7/1999 | Green | 600/160 |
| 5,947,958 A | 9/1999 | Woodward et al. | |
| 5,961,445 A | 10/1999 | Chikama | |
| 5,984,861 A | 11/1999 | Crowley | |
| 6,013,025 A | 1/2000 | Bonne et al. | 600/160 |
| 6,059,720 A | 5/2000 | Furusawa et al. | |
| 6,086,542 A | 7/2000 | Glowa et al. | |
| 6,086,554 A | 7/2000 | Humphreys, Jr. et al. | |
| 6,179,776 B1 | 1/2001 | Adams et al. | |
| 6,190,353 B1 * | 2/2001 | Makower et al. | 604/95.01 |
| 6,275,255 B1 | 8/2001 | Adair et al. | 348/76 |
| 6,293,910 B1 | 9/2001 | Yamakita et al. | |
| 6,306,083 B1 | 10/2001 | Bonne et al. | 600/182 |
| 6,310,642 B1 | 10/2001 | Adair et al. | 348/76 |
| 6,322,498 B1 | 11/2001 | Gravenstein et al. | |
| 6,350,231 B1 | 2/2002 | Ailinger et al. | |
| 6,387,044 B1 | 5/2002 | Tachibana et al. | |
| 6,393,431 B1 | 5/2002 | Salvati et al. | 707/104.1 |
| 6,411,835 B1 | 6/2002 | Modell et al. | |
| 6,432,047 B1 * | 8/2002 | Gust et al. | 600/182 |
| 6,478,730 B1 * | 11/2002 | Bala et al. | 600/121 |
| 6,487,440 B2 | 11/2002 | Deckert et al. | |
| 6,503,196 B1 | 1/2003 | Kehr et al. | |
| 6,527,704 B1 | 3/2003 | Chang et al. | 600/112 |
| 6,530,881 B1 | 3/2003 | Ailinger et al. | |
| 6,549,794 B1 | 4/2003 | Nadeau, Jr. et al. | |
| 6,561,973 B1 | 5/2003 | Bala | 600/178 |
| 6,599,238 B2 | 7/2003 | Ooshima et al. | |
| 6,612,981 B2 | 9/2003 | Onishi et al. | |
| 6,659,940 B2 | 12/2003 | Adler | 600/109 |
| 6,695,772 B1 | 2/2004 | Bon et al. | |
| 6,712,757 B2 | 3/2004 | Becker et al. | |
| 6,730,019 B2 | 5/2004 | Irion | |
| 6,740,030 B2 | 5/2004 | Martone et al. | |
| 6,761,684 B1 | 7/2004 | Speier | |
| 6,761,685 B2 | 7/2004 | Adams et al. | |
| 6,808,505 B2 | 10/2004 | Kadan | |
| 6,826,422 B1 | 11/2004 | Modell et al. | |
| 6,863,651 B2 | 3/2005 | Remijan et al. | 600/130 |
| 6,936,004 B2 | 8/2005 | Utsui | |
| 6,955,644 B2 | 10/2005 | Forkey et al. | |
| 2001/0000040 A1 | 3/2001 | Adams et al. | |
| 2002/0013513 A1 | 1/2002 | Bala | 600/178 |
| 2002/0087047 A1 | 7/2002 | Remijan et al. | |
| 2003/0083552 A1 | 5/2003 | Remijan et al. | |
| 2003/0163030 A1 | 8/2003 | Arriaga | |
| 2003/0167000 A1 | 9/2003 | Mullick et al. | |
| 2004/0085441 A1 | 5/2004 | Onishi et al. | |
| 2004/0210107 A1 | 10/2004 | Tani et al. | |
| 2005/0215859 A1 | 9/2005 | Chin et al. | |
| 2005/0234298 A1 | 10/2005 | Kucklick et al. | |
| 2005/0267330 A1 | 12/2005 | Deppmeier et al. | |
| 2007/0021713 A1 | 1/2007 | Kumar et al. | |

FOREIGN PATENT DOCUMENTS

| | | |
|---|---|---|
| EP | 0 072 205 | 2/1983 |
| EP | 0 316 244 | 5/1989 |
| EP | 0 461 669 | 12/1991 |
| EP | 0549097 | 6/1993 |
| EP | 0 586 162 | 3/1994 |
| EP | 0 647 425 | 4/1995 |
| GB | 2 339 922 | 2/2000 |
| JP | 01-204642 | 8/1989 |
| JP | 04-177310 | 6/1992 |
| JP | 05-317241 | 12/1993 |
| JP | 06-202007 | 7/1994 |
| JP | 08-110486 | 4/1996 |
| JP | 09-178446 | 7/1997 |
| JP | 00-097846 | 4/2000 |
| JP | 01/264644 | 9/2001 |
| WO | WO 92/22238 | 12/1992 |
| WO | 94/14367 | 7/1994 |
| WO | WO 96/39916 | 12/1996 |
| WO | WO 97/09937 | 3/1997 |
| WO | 99/35960 | 7/1999 |
| WO | WO 00/03272 | 1/2000 |
| WO | WO 00/13568 | 3/2000 |
| WO | 01/19235 | 3/2001 |
| WO | 01/22866 | 4/2001 |
| WO | WO 03/034905 | 5/2003 |
| WO | WO 2005/112736 | 12/2005 |

* cited by examiner

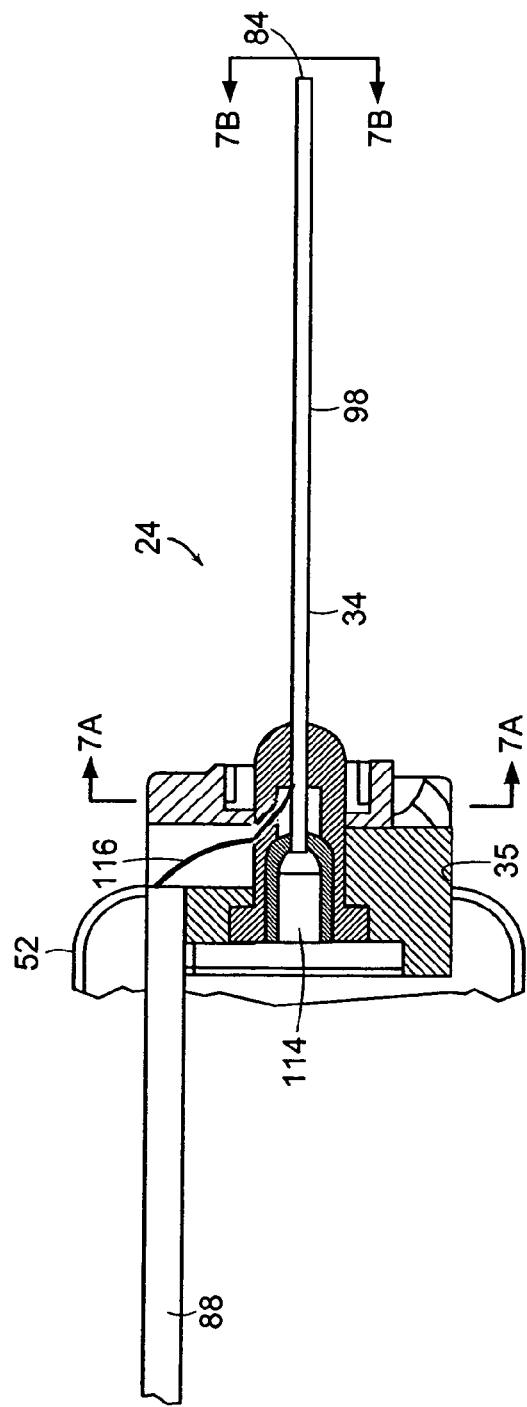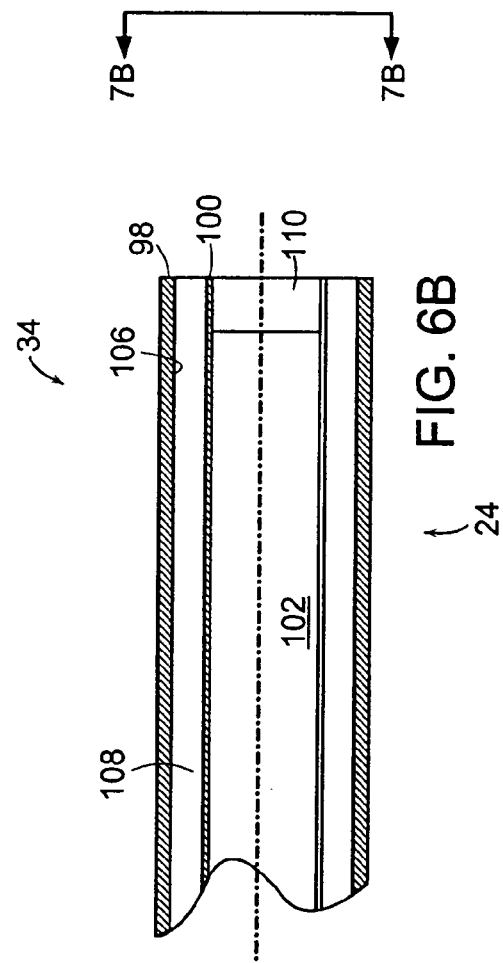

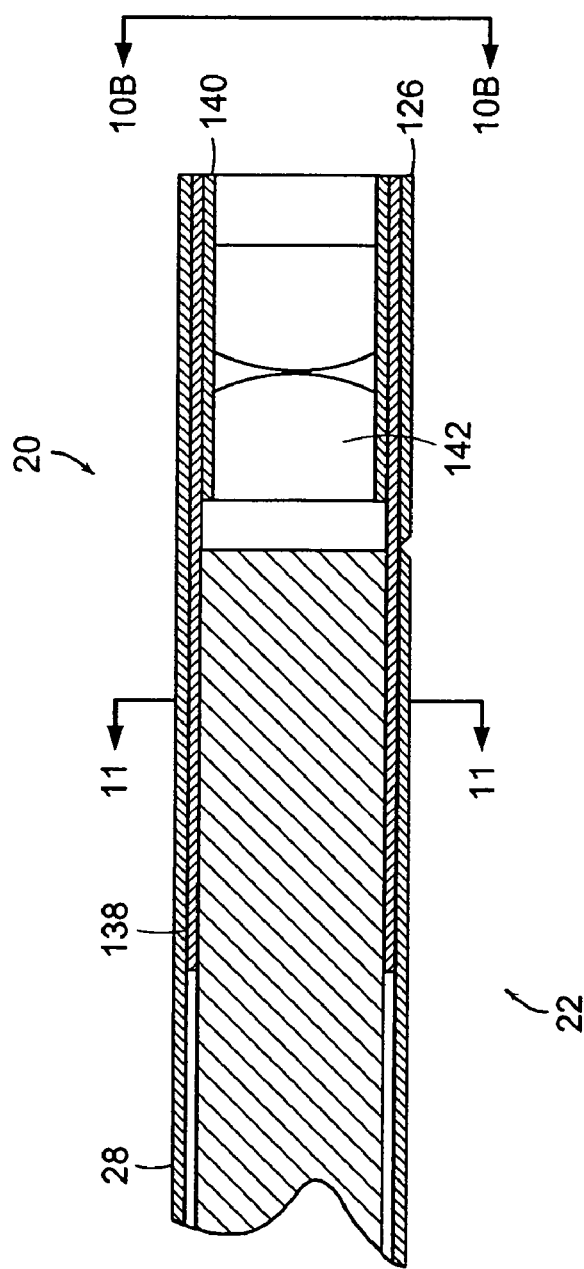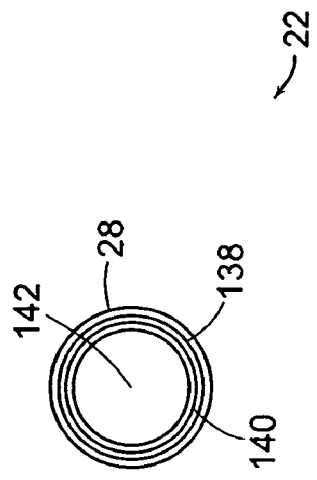
FIG. 10A
FIG. 10B

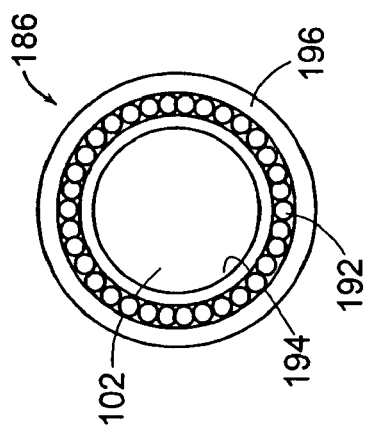
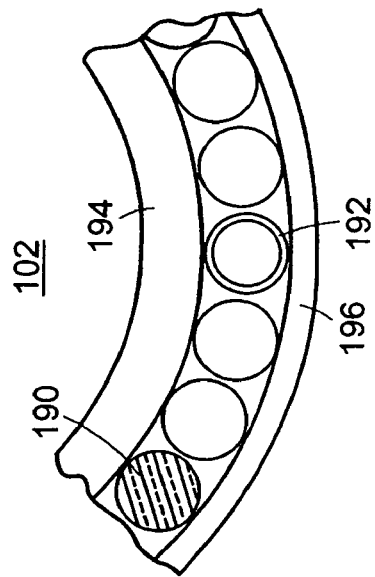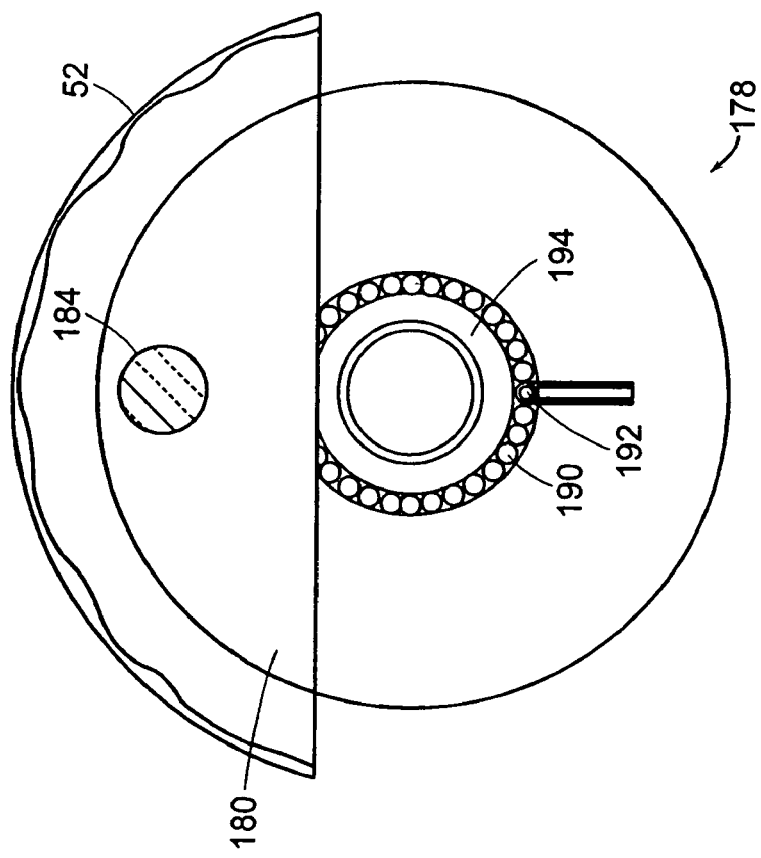
FIG. 16B
FIG. 16C
FIG. 16A

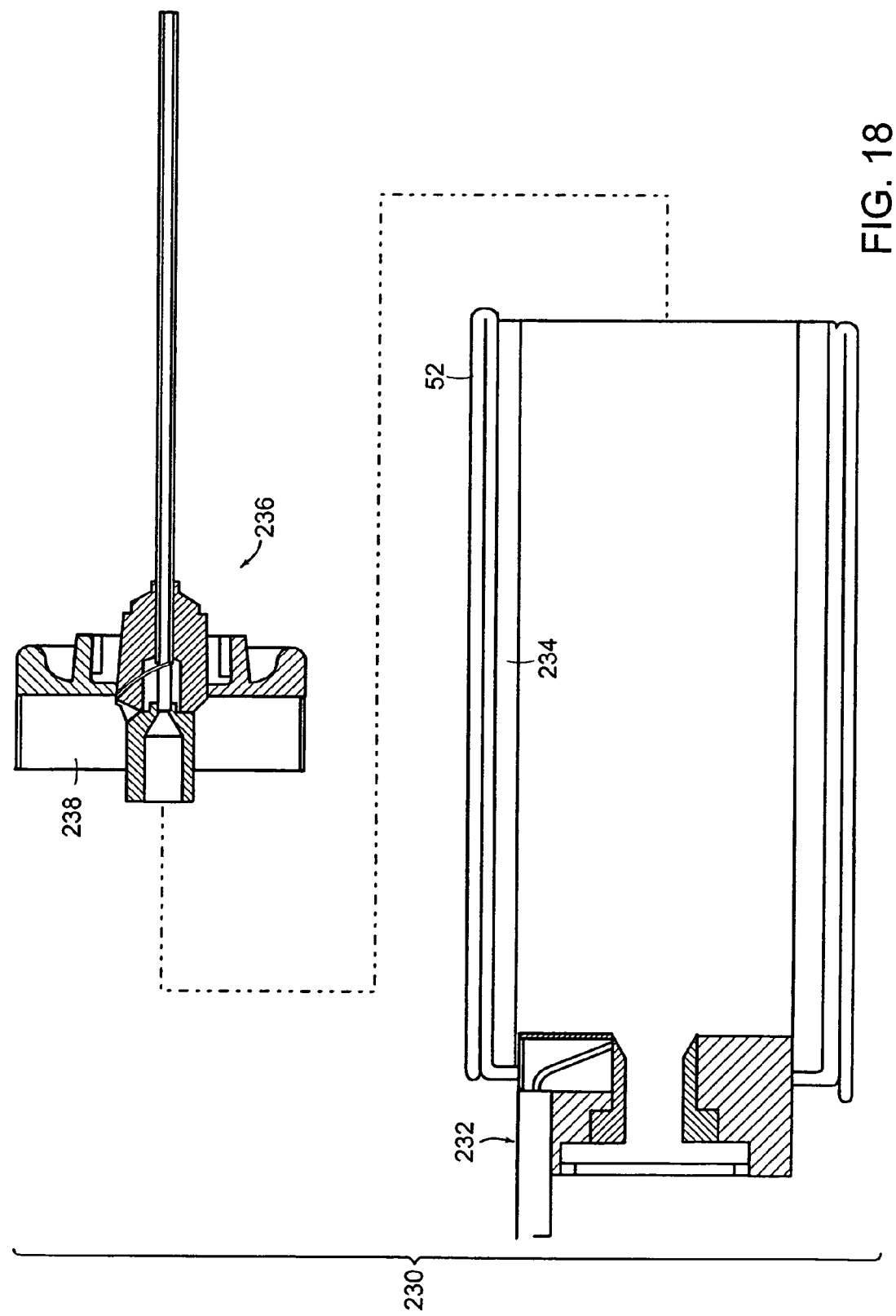

MINIATURE ENDOSCOPE WITH IMAGING FIBER SYSTEM

CROSS REFERENCE TO RELATED APPLICATIONS

This application is a continuation of U.S. application Ser. No. 10/042,126 filed on Oct. 19, 2001 now U.S. Pat. No. 6,863,651, the entire contents of this application being incorporated herein by reference.

BACKGROUND OF THE INVENTION

Endoscopes enable visual examination of structure inside cavities. In the field of medicine, the use of endoscopes permits inspection of organs for the purposes of diagnosis, viewing of a surgical site, sampling tissue, or facilitating the safe manipulation of other surgical instruments.

Laparoscopes, for example, are used particularly for examining organs in the abdominal area. Laparoscopes typically include a light pipe for illuminating the region to be viewed, at least one lens assembly for focusing and relaying the image of the illuminated object, and a housing for the entire assembly which is structured to minimize tissue damage during the surgical procedure. The light pipe can include a fiber optic element for illuminating the site. The laparoscope housing includes a distal section that can be inserted within a body cavity and a proximal section which can include a handle that a user grips to position the distal end near the surgical site.

Existing endoscopes can include an imaging device such as a charged coupled device (CCD). This device can capture an image of an object being viewed and convey it to a display device, such as a monitor. There is a continuing need to improve on the operational features and manufacturability of endoscope systems that improve imaging capability and reduce the risk to the patient.

SUMMARY OF THE INVENTION

The present invention relates to a small diameter imaging probe or endoscope having improved durability, resolution, and field of view. In a preferred embodiment of the invention, the distal end of the probe including a disposable sheath, can be inserted into the tissue under examination. The probe is less than 3 millimeters in diameter, and preferably less than 2 millimeters in diameter, to reduce trauma at the point of insertion and thereby provide access to sites that are otherwise unavailable for endoscopic procedures.

In a preferred embodiment, the endoscope has a fiber optic waveguide that transmits an image from a distal end to a proximal end. A lens system is positioned at the distal end of the fiber optic waveguide. An imaging device is optically coupled to the proximal end of fiber optic waveguide. A sheath extends about the fiber optic waveguide, the sheath including illumination fibers. Although a preferred embodiment utilizes a probe and sheath assembly having an outer diameter of 2 mm or less, certain applications will accommodate a larger diameter instrument having a larger number of imaging fibers to provide a higher resolution image. These applications can utilize outer diameters in a range of 2-4 mm.

In one embodiment, the lens system having a first lens element, a second lens element and an aperture stop. The lens system couples light from any given position on the object to a plurality of optical fibers such that the numerical aperture of light varies as a function of the angle relative to the longitudinal axis of the lens system. This provides more efficient coupling to the fiber apertures. This is accomplished using a non-telecentric lens system.

A preferred embodiment of the lens system includes a pair of lenses and an aperture stop. The lenses are shaped to improve light collection around the periphery of the distal lens. This provides a clearer image across the entire field of view of the device. The aperture stop is positioned to provide efficient coupling to the array of fibers.

The imaging device can be a charged coupled device (CCD), a CMOS imaging device or other solid state imaging sensor having a two dimensional array of pixel elements. The imaging sensor is mounted on a circuit board in a handle assembly. The sensor can capture an image as an object being viewed and an image processing circuit mounted onto the circuit board transfers the image data over a video cable to a computer for storage, processing and/or display.

The miniature endoscope system can be used for orthopedic, rhematologic, general laparoscopic, gynecological or ear, nose and throat procedures, for example. Although many applications require a small diameter to reduce trauma, certain applications can accommodate larger diameters. The probe can include an open channel in either the sheath or the imaging probe to provide for the insertion of other operative elements to flush the site with fluid, direct light or other energy source onto a treatment site, or to remove a tissue sample.

The sheath assembly can include a concentric array of illumination fibers extending to a connector on a sheath hub assembly. Alternatively, the illumination fibers can couple to a fiber connector in the probe assembly that is coupled directly via fiber optic cable extending from the handle to a light source housing. The housing can include a video disk recorder that writes the video onto disk. For certain applications, an illumination bundle can be positioned within the probe such that the sheath is thinner or can accommodate a larger working channel.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 6A is a sectional view of the disposable sheath/illuminator unit;

FIG. 6B is an enlarged sectional view of the distal end to the disposable sheath;

FIG. 10A is an enlarged view of the distal end of the imaging unit as indicated by the portion defined 10A in FIG. 9;

FIG. 10B is a front view of the distal end of the imaging unit taken along the line 10B-10B of FIG. 10A;

FIG. 16A is a sectional view of the endoscope taken along line 16A-16A of FIG. 15;

FIG. 16B is a sectional view of the endoscope taken along line 16B-16B of FIG. 15;

FIG. 16C is an enlarged sectional view of the imaging unit as indicated by the portion defined by 10C in FIG. 16B;

FIG. 18 is a side view of a two-part disposable sheath/illuminator unit;

DETAILED DESCRIPTION OF THE INVENTION

Figure 1:
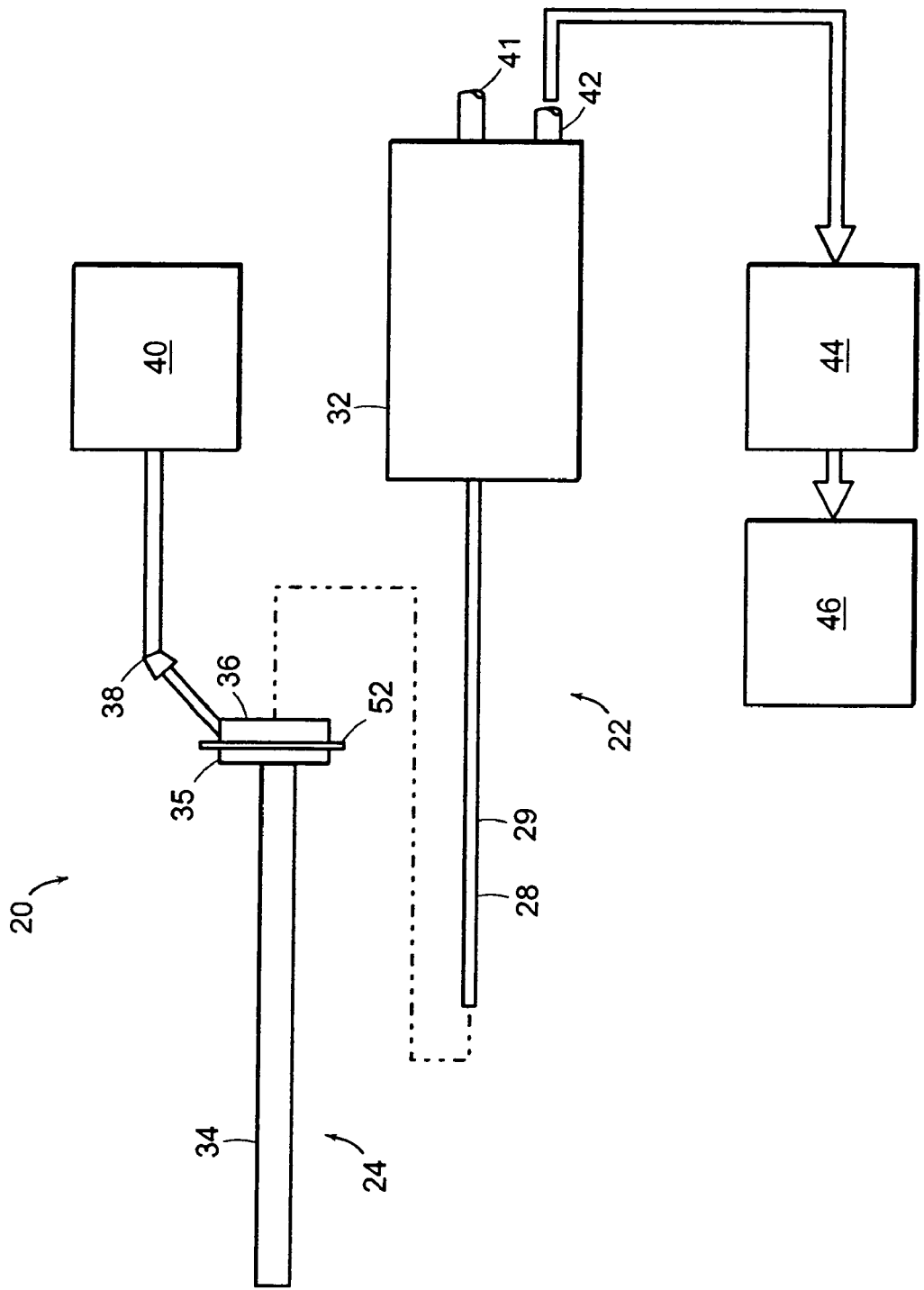
FIG. 1 illustrates a schematic illustration of a miniature endoscope system according to the invention.
Figure 9:
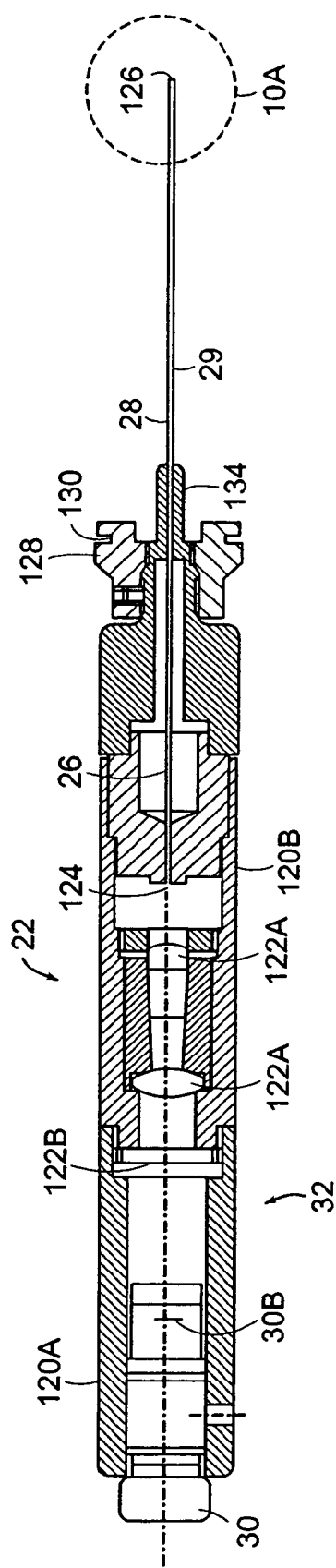
FIG. 9 is a sectional view of an imaging unit of the miniature endoscope.

An embodiment of the invention is illustrated in FIG. 1 that shows a miniature endoscope 20. The endoscope 20 has an imaging unit 22 and a sheath/illuminator unit 24. The endoscope 20 has an image transmission path such as a plurality of optical fibers 26, as best seen at fibers 146 in FIGS. 11 and 12, in an elongated tube 28 of a rod tip 29 used to view objects to be examined. The optical fibers 26 are optically coupled to an imaging device 30, such as a charged coupled device as seen in FIG. 9, or other pixilated flat panel sensor, in a handle 32. A disposable sheath 34 of the sheath/illuminator unit 24 overlies the elongated tube 28 of the rod tip 29, which contains the optical fibers 26. The disposable sheath 34 has at the proximal end a base 35 with a mounting mechanism 36 for securing to the handle 32. In one embodiment, the disposable sheath 34 of the sheath/illuminator unit 24 has a plurality of optical fibers for transmitting light to the distal end of the disposable sheath 34 and the distal probe 29. The distal end of the disposable sheath/illuminator unit 24 has a connection 38 to connect to a light source 40.

The handle 32 can house a power input 41, used to provide power to the endoscope 20. It is recognized that the light source 40 and/or power source can be mounted within the handle 32.

The handle 32 can also house an image output 42. The image output 42 provides a connection between an imaging device in the imaging unit 22 of the endoscope 20 and an electronic storage and/or display device. In one embodiment, the storage device is a computer 44, which is connected to a monitor 46. A control unit 250 is described in greater detail with respect to FIG. 19.

As explained below in greater detail the imaging unit 22 does not need to be sterilized in that the imaging unit 22 does not contact or is in direct exposure to the body. The sheath/illuminator unit 24 has the disposable sheath 34 that is a sleeve assembly 52 that is carried by the base 35 secured to the imaging unit 22 that overlies the elongated tube 28 to create a sterilized barrier. In addition, the sheath/illumination unit 24 has a sterilized drape 52 which is mounted to the base 35 of the sheath/illuminator unit 24 and is positioned to overlie the remaining portion of the imaging unit 22 to provide a sterile environment.

Endoscopes and endoscopes with disposable sheaths are described in PCT Application PCT/US00/25107 filed on Sep. 13, 2000 and U.S. patent application Ser. No. 09/518,954 filed on Mar. 6, 2000. The entire contents of the above applications are incorporated herein by reference in their entirety.

Prior to discussing the endoscope 20 in further detail, in order to use the endoscope 20, the endoscope 20 needs to be positioned in the body to view the desired location. One such method is to insert a cannula 60 into the body and thread the endoscope 20 through the cannula 60. One method of inserting the cannula 60 into the body and then inserting the endoscope 20 into a body using the cannula 60 is described below.

Figure 2:
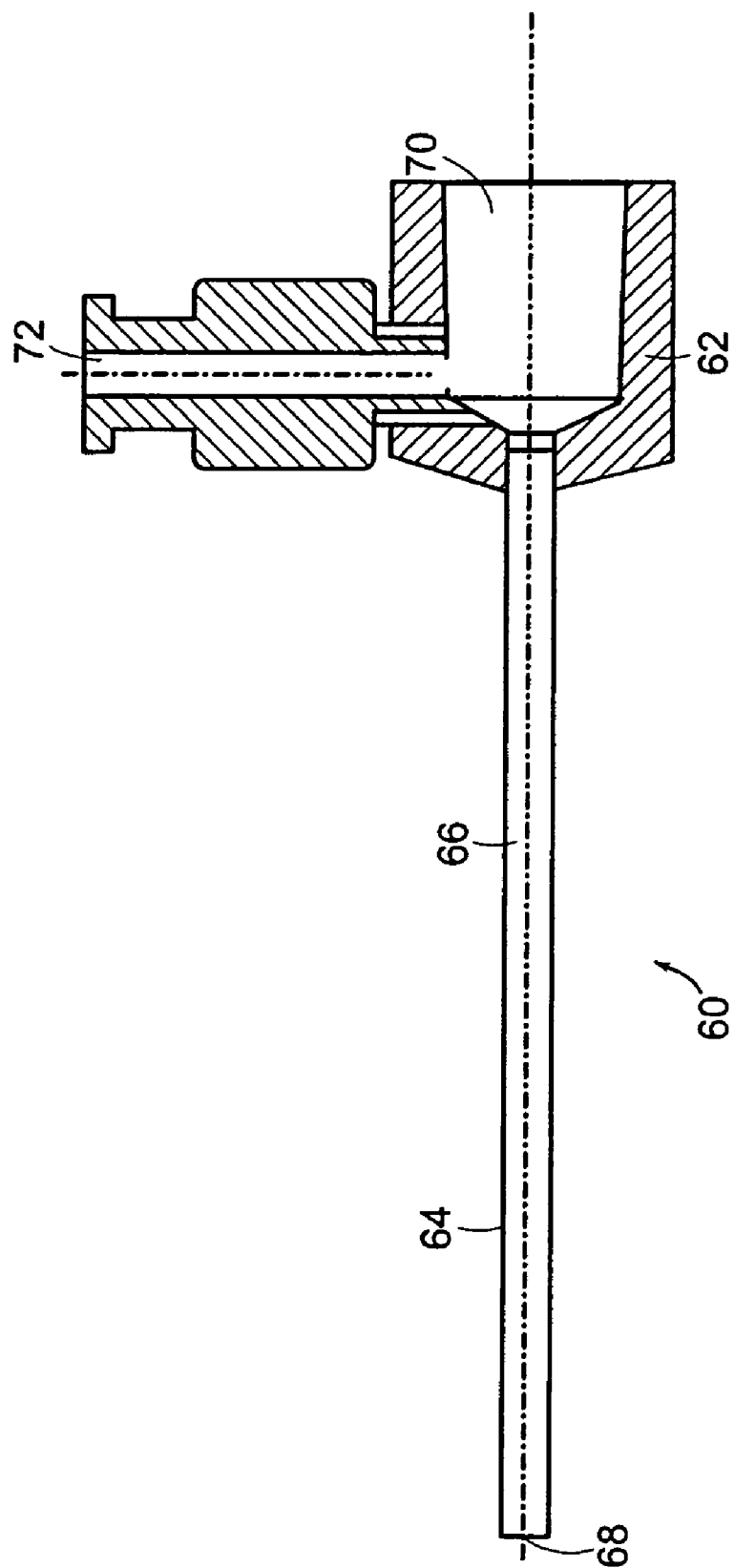
FIG. 2 is a cross-sectional view of cannula.

During an insertion procedure, a cannula 60 such as seen in FIG. 2, is first inserted into a site within a body. The cannula 60 has a base 62 and a tube 64. The tube 64 has a shaft 66 which extends from the distal end 68 to a void 70 in the base 62. In one embodiment, the tube 64 is made of a flexible material such as plastic or thin wall stainless steel. The cannula 60 has a luer 72 for insertion of medications or fluids or for attachment to a suction device.

Figure 3:
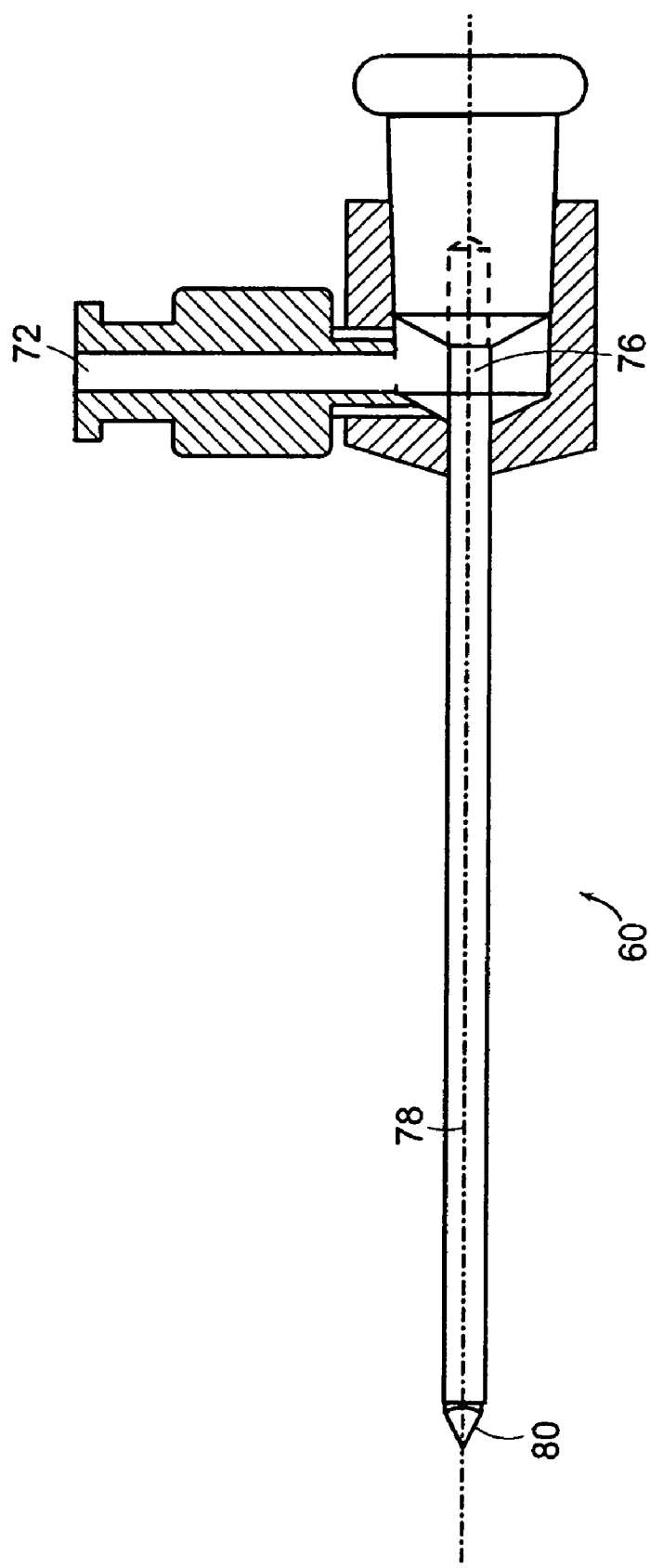
FIG. 3 is a cross-sectional view of a trocar within a cannula.

For insertion of the cannula 60 into the body, a trocar 76, as seen in FIG. 3, is inserted into cannula 60 with a rigid shaft 78 of the trocar 76 received within the shaft 66 of the cannula 60. The rigid shaft 78 of the trocar 76 extends slightly beyond the distal end of the tube 64 of the cannula 60 and has a stylet 80 to cut into the tissue at the surgical site if necessary. Once the cannula 60 is positioned at the surgical site, the trocar 76 is removed from the cannula 60 and the endoscope 20 is installed. The cannula 60 is positioned by the user's hands feeling the location.

While the cannula 60 and trocar 76 are of a relative minimal cost and can be reused after sterilization or disposed of after use, because of several components in the endoscope 20 such as components in the imaging unit 22, it is not desirous to dispose of the entire endoscope 20. The endoscope 20 uses a disposable sleeve or sheath 34 to aid in maintaining a sterile environment and reduce or eliminate the sterilization requirements prior to reuse.

Figure 4:
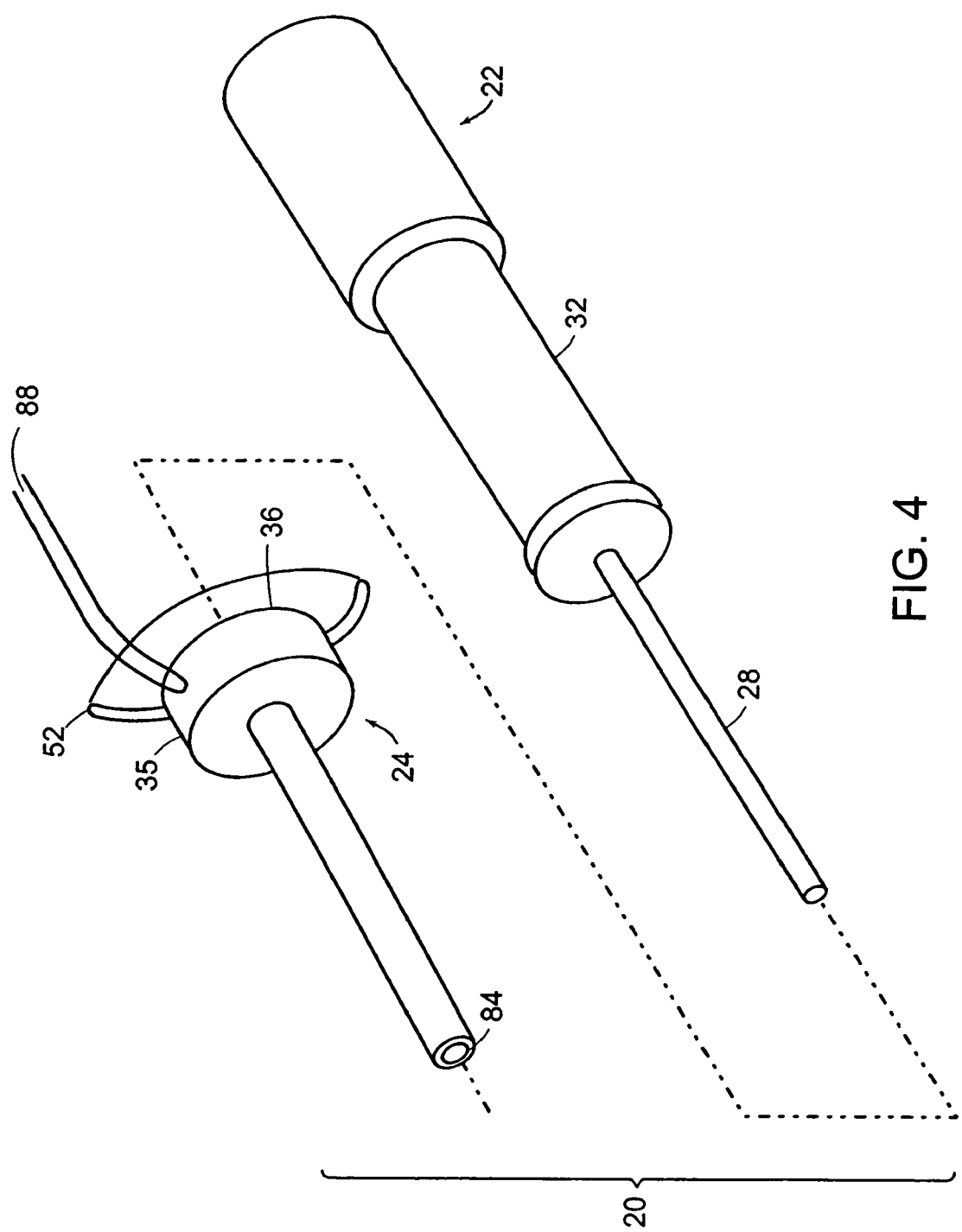
FIG. 4 is a perspective view of the miniature endoscope.

With the method of inserting the endoscope 20 into the cannula 60 to have the distal end of the endoscope 20 at the proper location, previously described, the endoscope 20 is described in further detail. Referring to FIG. 4, a perspective view of the endoscope 20 is shown. The endoscope 20 has the reusable imaging unit 22 and the disposable sheath/illuminator unit 24. The disposable sheath/illuminator unit 24 has a elongated tube for overlying and encircling the elongated tube 28 of the imaging unit 22. The elongated tube of the sheath/illuminator unit 24 has a sealed distal end 84 and several embodiments includes fiber optics for transmitting the illumination from a external light source 40, such as seen in FIG. 1, to the distal end 84. At the proximal end of the sheath/illuminator unit 24 is a base 35 with a mounting mechanism 36 for securing to the imaging unit 22 of the endoscope 20. An optical pigtail 88 projects from the base 35 for connecting to the light source 40. In addition, the sheath/illuminator unit 24 has a the drape 52 which is mounted to the base 35 and is extended over the handle 32 of the imaging unit 22. The handle 32 of the imaging unit 22 contains optics and the imaging device 32 to receive the image transmitted through the optical fibers 26 located in the elongated tube 28 of the imaging unit 22 as described in further detail below with respect to FIGS. 9-11.

Figure 5:
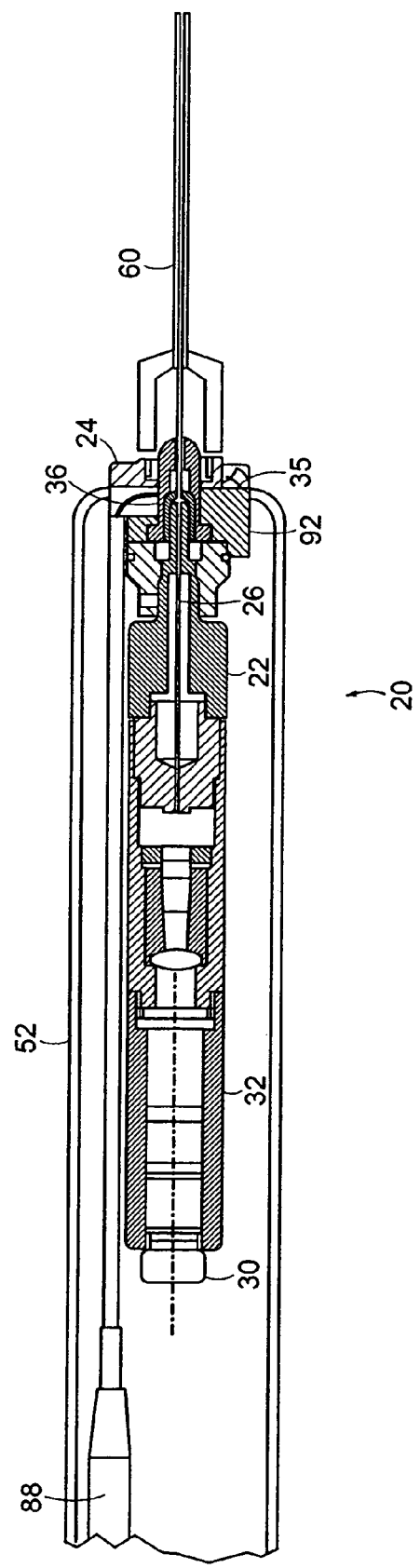
FIG. 5 is a sectional view of the miniature endoscope with a cannula overlying the disposable sheath.

FIG. 5 is a sectional view of the miniature endoscope 20 including the reusable imaging unit 22 with imaging an optical fiber 26 and the disposable sheath/illuminator unit 24. The cannula 60 is shown overlying the disposable sheath 34 of the sheath/illuminator unit 24, which overlies the probe 29 of the imaging unit 22.

As seen in FIG. 5, the reusable imaging unit 22 of the endoscope 20 is encircled by the disposable sterile sheath/illuminator unit 24. The disposable/sheath illuminator unit 24 has the disposable sheath 34 that is sealed at the distal end 84 and encircles and surrounds the elongated tube 28 carrying the optical fibers 26 of the imaging unit 22. The mounting mechanism 36 on the base 35 of the sheath/illuminator unit 24 is secured to a mounting mechanism 92 on the imaging unit 22.

The disposable sheath/illuminator unit 24 has the drape 52 which surrounds the handle of the imaging unit 22. In addition, the sheath/illuminator unit 24 has the illumination pigtail connecting to a light source 40 as seen in FIG. 1. The illumination pigtail 88 is optically coupled to the optical fibers in the sheath as explained in further detail below.

Referring to FIG. 6A, a side view of the sheath/illuminator unit 24 is shown. The sheath unit 24 has the disposable sheath 34 with an elongated outer sheath 98 which extends from the base 35 to the distal end 84. The illuminator pigtail 88 extends from the base and is optically coupled to illumination fibers within the sheath 34 as seen in FIG. 7A. The drape 52 is carried by the base 35 of the sheath/illuminator unit 24 for overlying the handle 35 of the imaging unit 22 when the two units 22 and 24 are combined.

FIG. 6B is an enlarged view of the distal end 84 of the disposable sheath 34 of the sheath/illuminator unit 24. The disposable sheath 34 has the outer sheath 98 which extends from within the base 35, as seen in FIG. 6A, and serves as protective covering and a sterile barrier for the sheath unit 24. Spaced and collinear with the outer sheath 98 is an inner tube 100 of the disposable sheath 34. The inner tube 100 defines a cylindrical void on space 102 for receiving the elongated tube 28 of the probe 29 of the imaging unit 22. The inner tube 100 likewise from the distal end 84 of the disposable sheath 34 to the base 35 of the sheath/illuminator unit 22. The inner tube 100 extends further than the outer sheath 98 to create a channel 106 to receive a plurality of illumination fibers 108 as best seen in FIGS. 6A and 7A. At the distal end, of the inner tube 100 is located a window 110 which is secured to the inner tube 100 to make a sterile 84 barrier between the airspace 102 for receiving the elongated tube 28 of the image unit 22 and the outer portion of the sheath/illuminator unit 24 which is in contact with the body.

In a preferred embodiment, the outer sheath 98 of the disposable sheath 34 of the sheath/illuminator unit 24 is made of a stainless steel material and has an outer diameter of about 0.038 inches. The inner tube 100 is likewise made of a stainless steel material. The illumination fibers 108 are made of a glass or plastic fiber. Depending on the size of the device, the maximum number of illumination fibers 108 used to fill channel 106. In one example, the disposable sheath 34 extends 2.246 inches from the base 35 of the sheath/illuminator unit 24.

Figure 7B:
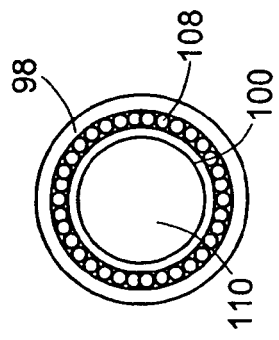
FIG. 7B is a front view of the distal end of the disposable sheath taken along the line 7B-7B of FIG. 6A and FIG. 6B.
Figure 7A:
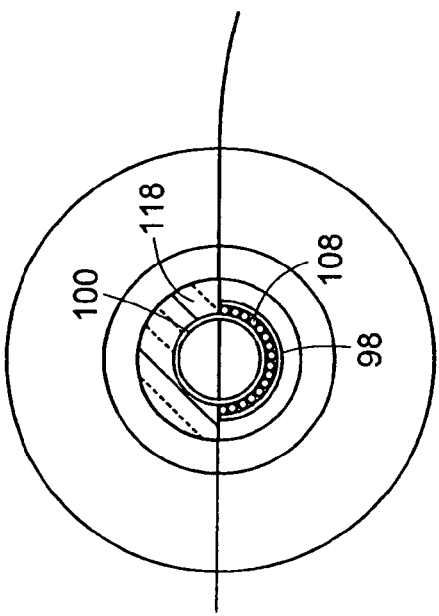
FIG. 7A is a sectional view of the proximal end of the disposable sheath/illumination unit taken along line 7A-7A of FIG. 6A.

Interposed between the outer sheath 98 and the inner tube is the plurality of illumination fibers 108 which encircle the inner tube 100 as best seen in FIGS. 7A and 7B. FIG. 7A is a sectional view through the base 35 of the disposable sheath 24. The outer sheath 98 is shown in the lower half of FIG. 7A and terminates prior to the portion sectioned in the upper half of FIG. 7A. The inner tube 100, however, which defines the airspace 102 to receive the elongated tube 28 of the imaging unit 22 extends to a receiving chamber 114 as seen in FIG. 6A and therefore is shown in both the upper and lower portions of FIG. 7A. The light is transmitted from the illumination pigtail 88 through fibers 108, as seen in FIG. 6A, to a transmission unit 118 as seen in the upper half of FIG. 7A which abuts the illumination fibers 108 located between the outer sheath 98 and the inner tube 100 of the disposable sheath 34 of the sheath/illuminator unit 24.

FIG. 7B shows the distal end 84 of the disposable sheath/illumination unit 24. The window 110 overlies and seals the airspace 102 that receives the imaging unit 22 and is encircled by the inner tube 100. Interposed between the outer sheath 98 and the inner tube 100 is the plurality of illumination fibers 108. In the embodiment shown, the distal end of the illumination fibers 108 are not protected and exposed to the body.

Figure 8:
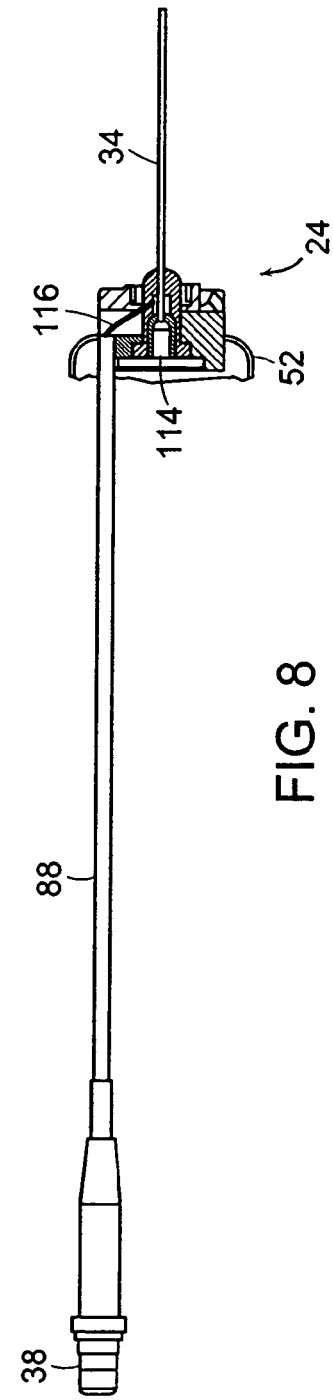
FIG. 8 is a side view of the disposable sheath/illumination unit showing the illumination pigtail.

FIG. 8 is similar to FIG. 6A in that it shows the disposable sheath/illumination unit 24. In addition, FIG. 8 shows the entire illumination pigtail which is broken away in FIG. 6A.

The illumination pigtail 88 has a connection 38 for connecting to a connector on the light source 40. The illumination pigtail 88 has a plurality of optical fibers which run from the connection 38 to the fibers 108 which transmit the light received from the light source 40 to the transmission unit 118 shown in FIG. 7A and exit at 84.

Referring to FIG. 9, a sectional view of the imaging unit of the endoscope 20 is shown. The imaging unit 22 has the probe 29 with the elongated tube 28 that extends from the handle 32. At the proximal end of the handle 32, is the imaging device. In this embodiment, a charged coupled device (CCD) 30B which converts the optical image into an electrical image is carried in the detachable housing 120A of the handle 32. Interposed between the optical fiber or fibers 26 which extend in the elongated tube 28 and the CCD 30B is a plurality of lenses 122A for projecting the image of the proximal end 124 of the optical fiber or fibers 26 to the CCD 30B. The glass window 122B is attached to housing 120B and provides a seal to the scope. It also protects the lenses from contamination.

The imaging unit 22 enlarges the image from the end of the fiber optic 26 and couples it to the charged coupled device 30B. As indicated above, the charged coupled device is connected to a electronic storage and/or display device such as a computer 44 which is connected to a monitor 46 as seen in FIG. 1.

The handle 32 of the imaging unit 22 has a mounting mechanism 128 for coupling with the mounting mechanisms 36 of the sheath illuminator unit 24. The mounting mechanism 128 has slots 130 for receiving pins located on the mounting mechanisms 36. In addition, the mounting mechanism 128 has a projection 134, from which the probe 29 projects, that is received by the receiving chamber 114 of the sheath/illuminator unit 24 as seen in FIG. 6A.

An enlarged view of the distal end of the imaging unit 22 is shown in FIG. 10A. The rod tip 29 of the imaging unit 22 has the elongated tube 28 that extends from the distal end 126 to the housing 120 of the handle 32. At the distal end 126 of the rod tip 29 there is in addition a tube 138 which extends a slight distance from the distal end 126 and just a slight distance beyond the ends of the optical or image fibers 26. The tube 138 is commonly referred to as the long tube in that a shorter and smaller diameter tube 140 which is collinear with the long tube 138 is received within the long tube 138 and extends a lens system 142 at the distal end 126. The elongated or outer tube 128, long tube 138 and small tube 140 are mounted so that their distal ends are flush and are secured by an adhesive such as a modicalgrade epoxy. At the end of the elongated tube 28 of the imaging unit 22 is the lens system 142 that is described in further detail below. The elongated tube 28 of the imaging unit 22 is received within the disposable sheath/illumination unit 24 and therefore does not need to be sterilized prior to the first use.

FIG. 10B is an end-view of the distal end 126 of the imaging unit 22. The lens system 142, the small tube 140, the long tube 138 and the outer or elongated tube 28 are shown and are all collinear.

Figure 11:
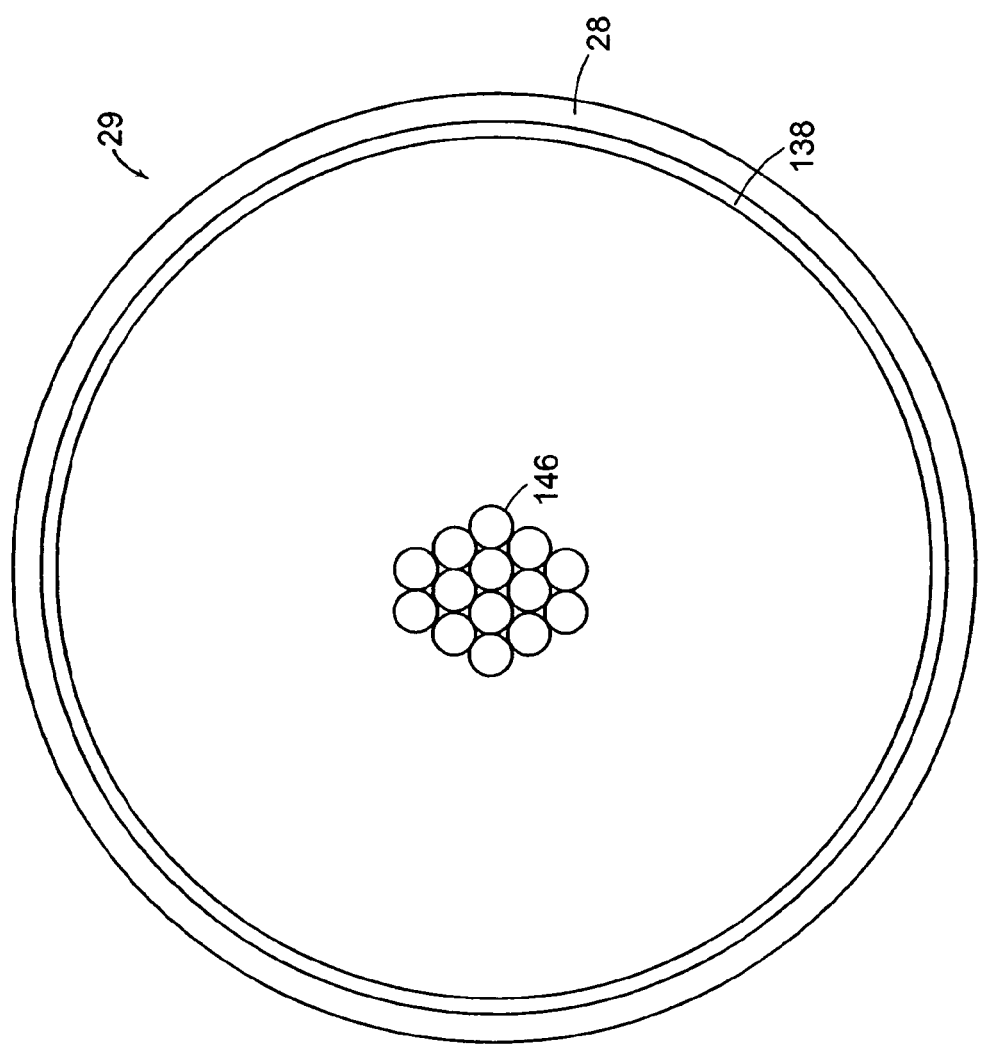
FIG. 11 is a schematic of an enlarged partial sectional view of the imaging unit taken along the line 11-11 of FIG. 10A.

Referring to FIG. 11, a sectional view of the imaging unit 22 of the endoscope 20 is shown. The probe 29 of the imaging unit 22 has a plurality of fibers 146 for transmitting the image from the distal end 126 of the rod tip 29 to the handle 32. Encircling the fiber 146 at the distal end of the rod tip 29 is the long tube 138 for holding the fibers 146 of the image fibers 26 in position. The outer or elongated tube 28 encircles the long tube 138 and protects the fibers 146 of the image fibers 26 from their beginning near the distal end 126 of the rod tip 29 to the other end within the handle 32. There are typically thousands of fibers 146 as shown in FIG. 11 that are fused together. The loading of the image into them is done by the distal end lens system 142 which as described below arranges the light levels of the image in a relationship to the location of the image fiber bundle 26.

In addition, the fibers are in a disorder pack method. This disorder pack method limits transmission of images/light from one lens 142 to another as the image fiber bundle 26 extends from near the distal end 126 of the imaging unit 22 towards the proximal end of the fibers located within the handle 32. The disorder packing of fibers is achieved by varying the doping of the fibers, which is the area to be examined.

Figure 12:
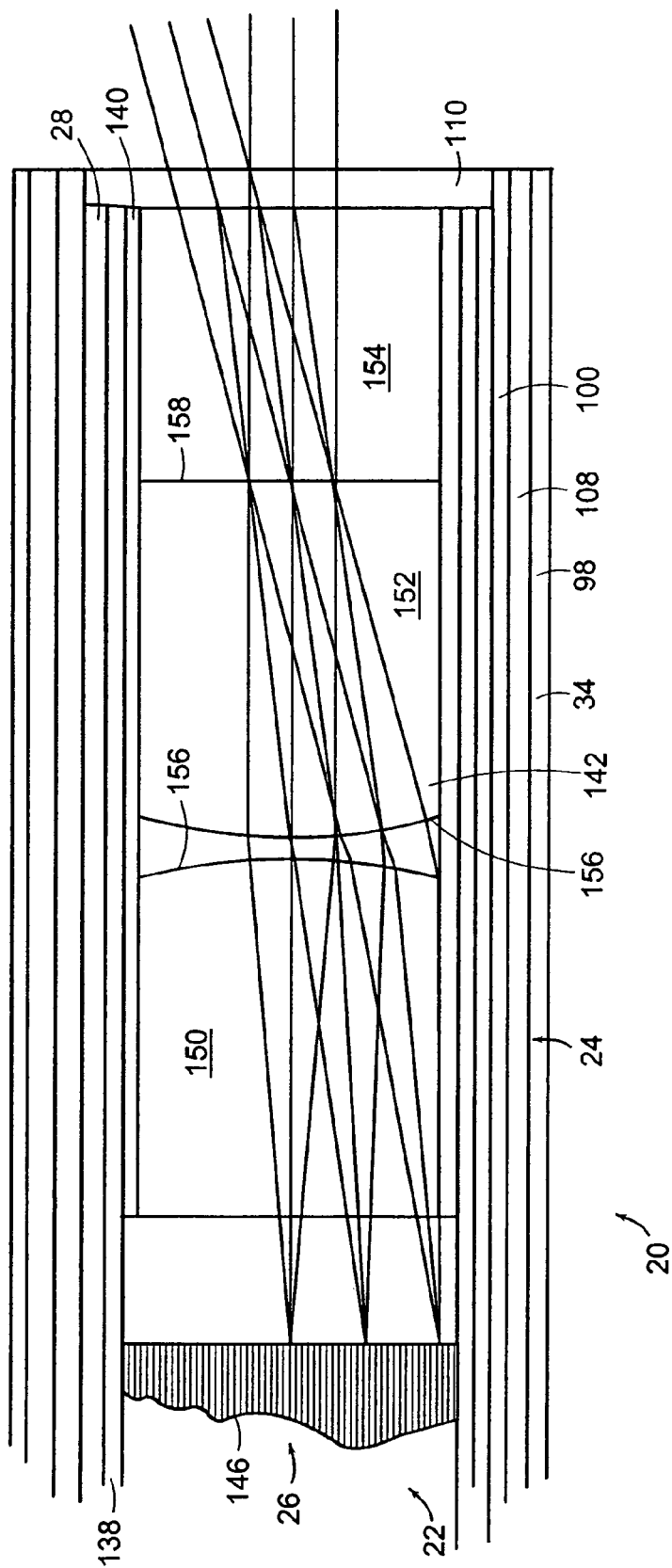
FIG. 12 is an enlarged view of the distal lens system.

Referring to FIG. 12, a sectional view of the distal end of the rod tip 29 of the imaging unit 22 within the disposable sheath 34 of the sheath/illuminating unit 24 is shown. The disposable sheath 34 has the outer sheath 98 collinear with the inner tube 100. Interposed between the outer sheath 98 and the inner tube 100 is the plurality of illumination fibers 108 as best seen in FIG. 7B for illumination. At the distal end of the disposable sheath is the window that is secured, such as by cementing, to create a boundary to the air space or inner channel 102 that receives the rod tip 29 of the imaging unit 22.

The imaging unit 22 has the elongated or outer tube 28 that extends from the distal end 126 to within the handle 32 as shown in FIG. 9. Located in the distal end 126 of the rod tip 29 are two additional tubes or sleeves, the shorter inner sleeve, referred to as the small tube 140, that retains and holds the lens elements of the distal lens system 142. A larger longer sleeve, referred to as the long tube 138, encircles the tube 140 and the beginning of the fibers 146 of the image fibers 26.

The distal lens system 142 as shown in FIG. 12 is an achromatic lens system having a pair of lenses 150 and 152 and an aperture stop 154. The lenses 150 and 152 each have a convex surface 156 that faces each other. The second lens 152, closer to the distal end 126, has a planar surface 158 which abuts the optical aperture stop 154. The aperture stop 154 and the lenses 150 and 152 are designed so that the sine of the maximum ray angle approaches the fibers at N.A. (numerical aperture).

The ray tracings 160 in FIG. 12 illustrate the projection of an image off the page to the right at the proper focal length and how this image is translated through the aperture stop 154 and through the lenses 152 and 150 to the plurality of fibers 146 in the image fibers 26. The lens system is non-telecentric.

Figure 13:
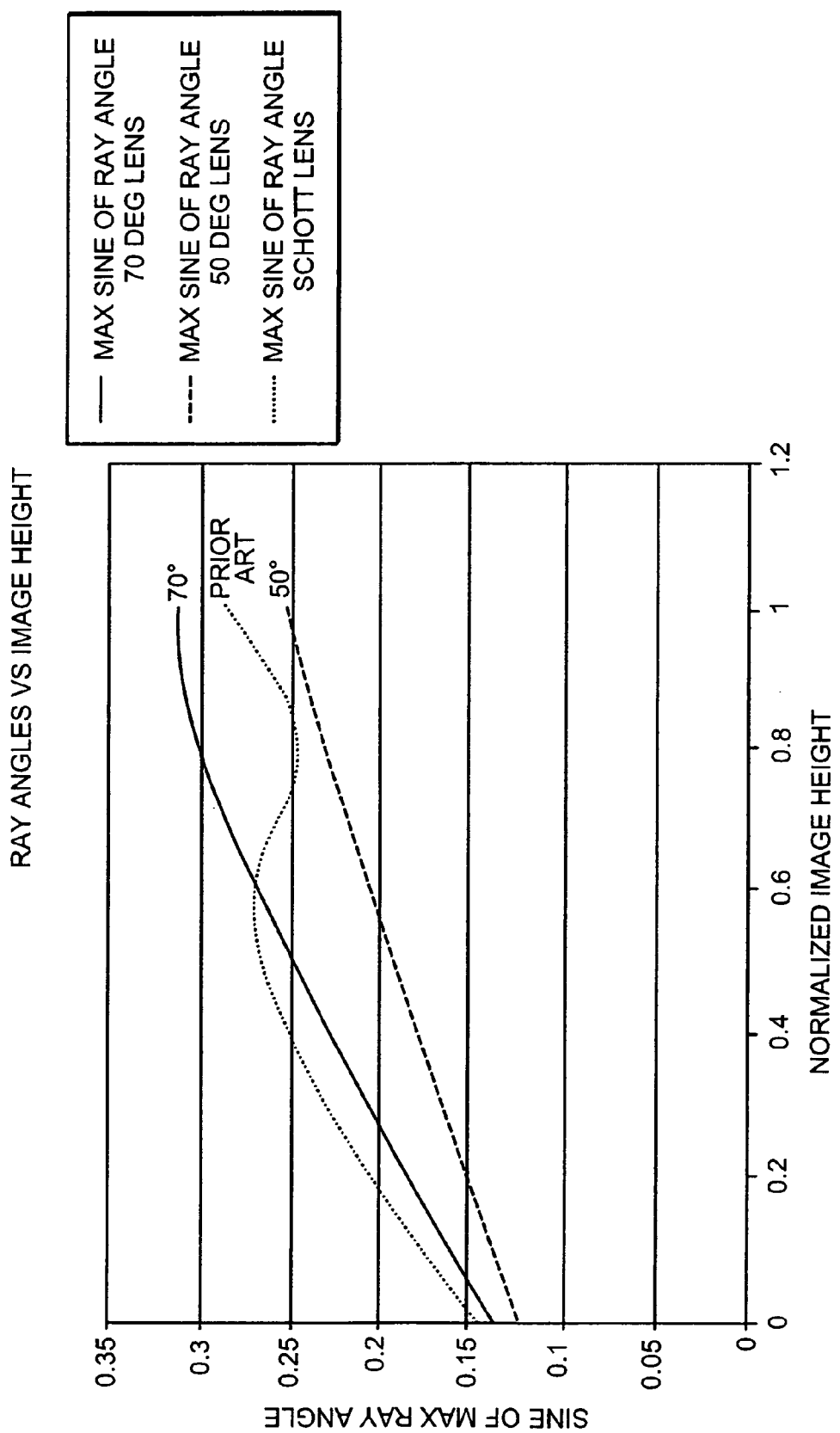
FIG. 13 is a graph of the sine of the maximum ray angle versus normalized image height for different lens systems for the distal end of the endoscope.

Referring to FIG. 13 a graph of the sine of the maximum ray angle versus the normalized image height for three different lens systems including a prior art lens system is shown. As discussed below, the field of view is dependent upon the lens configuration. The graph in FIG. 13 shows a line for the maximum sine of a ray angle for a 50 degree lens system and a second line for a maximum sine of ray angle of a 70 degree lens system. In the 70 degree system, the maximum sine is approximately 0.32. Therefore, the N.A. (numerical aperture) of the fiber is approximately the same. In contrast, the 50 degree field of view system has an sine of a maximum ray angle of approximately 0.25. Therefore, the fibers have this numerical aperture. The system can provide a field of view at any selected level from 30-80 degrees, for example.

In one embodiment, the endoscope 20 has 10,000 fiber elements. In this embodiment, each fiber element 146 has a diameter of 4.4 microns. The overall diameter of the fiber 26 is 0.46 mm. The elongated or outer tube 28 of the imaging unit is made from stainless steel. It is recognized, that the scope can be formed in many sizes, the following table is merely an illustration of various intervening size scopes.

|  | 3k | 10k | 30k | 50k | 100k |
|---|---|---|---|---|---|
| Sheath/Illumination unit outer diameter | 1-4 mm | | | | → |
| Imaging Unit rod tip outer diameter | 0.5-3.5 mm | | | | → |
| No. of fiber elements | 3,000 | 10,000 | 30,000 | 50,000 | 100,000 |
| Fiber image diameter | | 0.46 mm | 0.75 mm | | |
| Fiber pixel size (individual fiber) | 4.4 microns | 4.4 microns | 4.4 microns | | |
| Lens Type | Achromatic or Selfoc Grin | Achromatic or Selfoc Grin | Achromatic | Achromatic | Achromatic |
| Depth of Field (DOF) | | 3 mm-20 mm | | | → |
| Field of View (FOV) | Dependent on Lens 50°-70° | | | | → |

Figure 14:
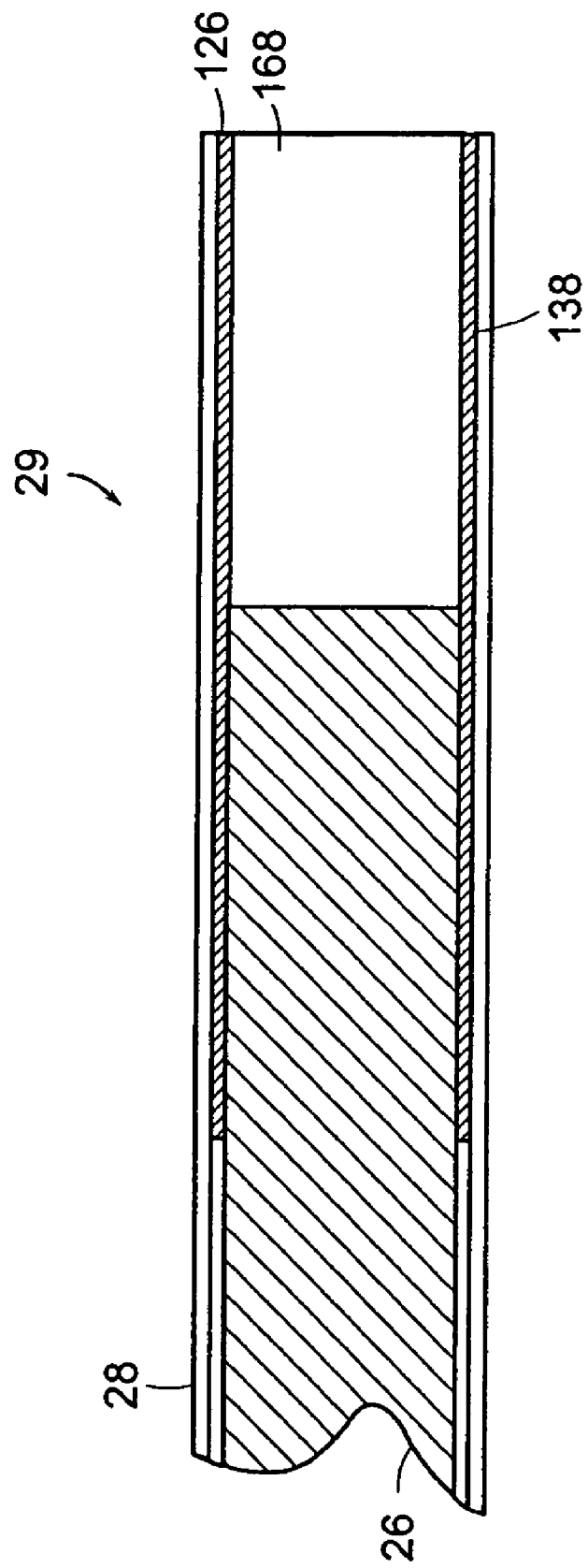
FIG. 14 is an enlarged view of another embodiment of a distal lens system.

As can be seen from table above, an alternative to an acromat lens described above with respect to FIGS. 12 and 13 is a selfoc grin lens. FIG. 14 shown an alternative embodiment of the rod tip 29 of the imaging unit 22 of the endoscope 20 with a grin lens 168. The grin lens 168 as shown in FIG. 14 is a single element gradient index lens.

The rod tip 29 of the image unit 22 as shown in FIG. 14 has an elongated or outer tube 28 that extends from the distal end 126 to the handle 32, not shown in FIG. 14. In addition, similar to that of FIG. 10A, a tube 138 extends a slight distance from the distal end 126. This tube 138 is commonly referred to as the long tube, it extends just slightly beyond the ends of the optical image fibers 26. In contrast to the embodiment shown in FIG. 10A in that the lens 170 is a single lens there is no need for a small tube 140 for retaining the elements of a lens system.

The grin lens 168 in general does not provide as good of image quality as that of the acromat lens system 142 described above in that the image becomes less clear (i.e., blurry and distorted) towards the edge of the image. In addition, the color correction, changes in intensity as a function of wavelength, is not as good as in the acromat lens system. However, the GRIN lens system 168 maybe desirable in situations where cost is a higher factor than the overall image quality. In addition, because of the grin lens 170 being a single element lens the depth of fields may be limited. While only 2 different degrees of freedom are shown, it is recognized that lens systems with other fields of view can be made.

Figure 15:
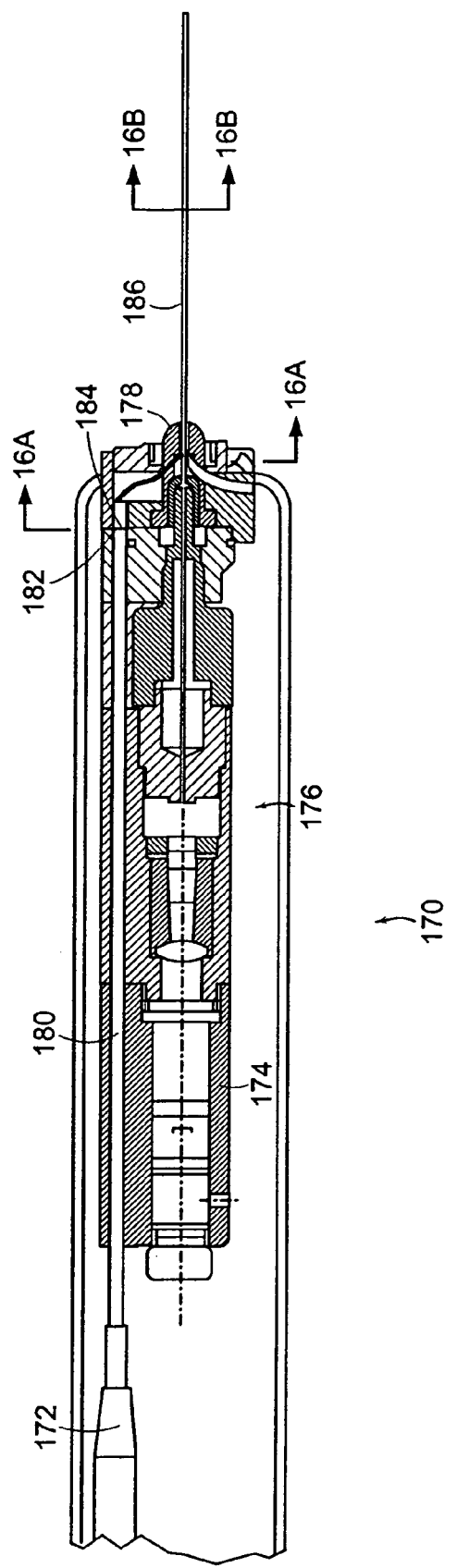
FIG. 15 is a sectional view of another embodiment of an endoscope.

FIG. 15 is a sectional view of alternative endoscope 170. In this embodiment of the endoscope 170, the illuminator pigtail 172 is a part of the handle 174 of the imaging unit 176 and is therefore not part of a disposable sheath/illuminator unit 178. An optical fiber bundle 180 is used for transmitting the illumination light from the pigtail 172 to a handle interface 182 in the handle 184 where the light is transferred to a light interface 184 on the sheath/illuminator unit 178 to transmit light from the handle 184 to the disposable sheath 186.

FIG. 16A is a sectional view showing the interface. FIG. 16A is a sectional view of the base 188 of the disposable/sheath illuminator unit 178. The upper portion of FIG. 16A shows the drape 52 spaced from the base 188. The base 188 has a light interface 184 that receives light from the handle interface 182 carried on the handle 174.

In addition in the embodiment of the endoscope 170 shown in FIGS. 16A-16C, the sheath/illuminator unit 178 has one of the illumination fibers 190 replaced by a tube or channel 192. The tube 192 which is seen in FIGS. 15 and 16A-16C is capable of receiving a laser fiber. The user passes a laser fiber though the tube 190 from the proximal end of the illumination unit 178 in the base 188 as seen in FIG. 15, to the distal end of the illumination unit so that the user while viewing the image through the imaging fibers and CCD can complete a process using the laser fiber.

The lower half of FIG. 16A shows a cross-sectional view through the base 188 of the sheath/illuminator unit 178 shows the tube 192 extending through the base into the annular ring containing the illumination fibers 190. Similar to that shown in FIG. 7A, FIG. 16A shows an inner tube 194 around which the illumination fibers 190 are located. The inner tube 194 defines an airspace through which the probe 29 of the imaging unit 176 of the endoscope 170 passes.

FIG. 16B is a sectional view of the disposable sheath 186 showing an outer tube 196 of the disposable sheath 186 and circling the illumination fibers 190 and a signal hypotube 192. The inner tube 194 surrounds the airspace 102 which receives the probe 29 of the imaging unit 176. FIG. 16C is an enlarged view showing the hypertube 192 with its opening to receive the laser fiber in the annular ray containing the illumination fibers 190 between the inner tube 194 and outer sheath 196.

While FIGS. 15-16C do not show a cannula 60, it is recognized in most uses of the endoscope 20 or 170, a cannula 60 can be used for extra protection of the endoscope 20 or 170.

Figure 17A:
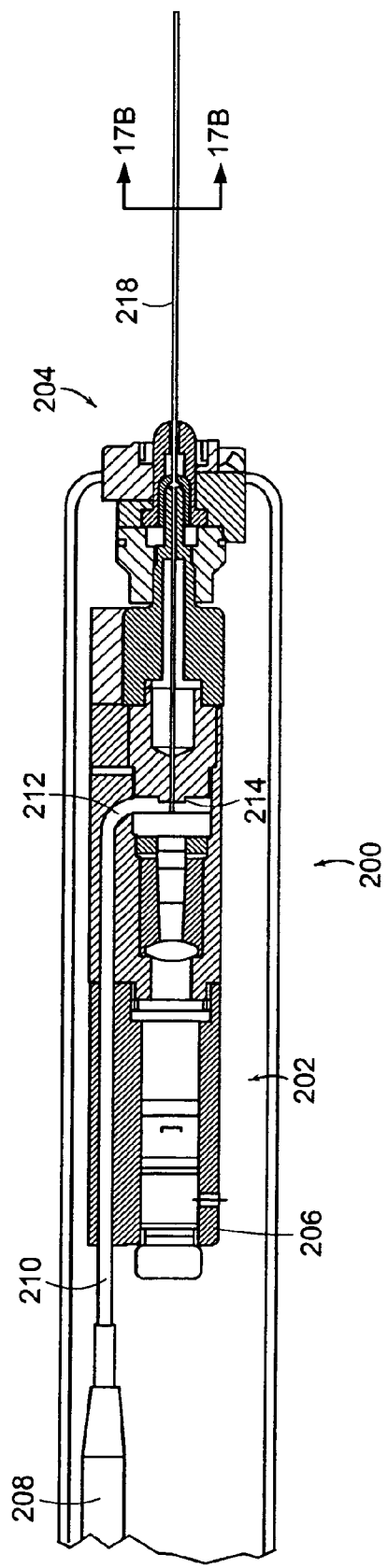
FIG. 17A is a sectional view of another embodiment of an endoscope.

Referring to FIG. 17A, a sectional view of an alternative endoscope 200 is shown. The endoscope 200 has an imaging unit 202 and a sheath unit 204. In contrast to the previous embodiments, the sheath 204 that is disposable does not include any part of the illumination unit. Referring to FIG. 17A, the illumination source 40 is connected to the handle 206 of the imaging unit 202 by an illumination pigtail 208 similar to that shown in FIG. 15. But in contrast, there is no coupling such that that the light is transmitted to the disposable sheath 204. Rather, as seen in FIG. 17A, the illuminator pigtail 208 is a part of the handle 206 of the imaging unit 202. An optical fiber 210 is used for transmitting the illumination light from the pigtail 208 to an interface 212 in the handle 206. The interface 212 is located within the handle 206 and transfer the light to an annular ring 214 of a plurality of illumination fiber 216.

Figure 17B:
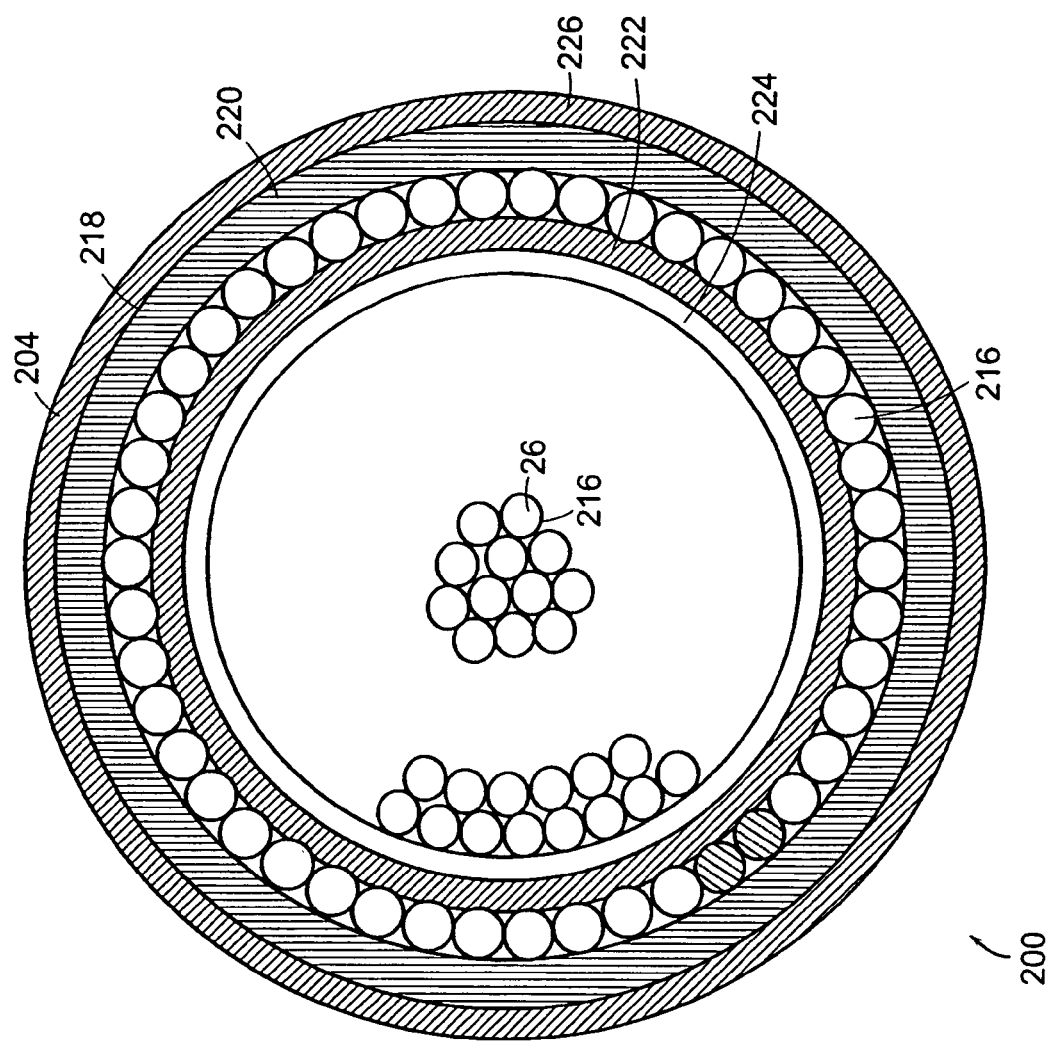
FIG. 17B is a sectional view of the endoscope taken along the line 17B-17B of FIG. 17A.

Referring to FIG. 17B, the probe 218 has an outer tube 220 and an inner tube 222. Interposed between the tubes 220 and 222 is the annular space for receiving the plurality of illumination fiber 216. Located in the inner tube 222, which is similar to the elongated tube 28 in the first embodiment, is the image fiber bundle 26. The fiber bundle 26 is spaced from the inner tube 222. A long tube 224, which extends for a slight distance from the distal end 126 to just beyond the ends of the image fiber bundle 26, is interposed between the fibers 26 and the inner tube 222.

In that the sheath is not required to carry illumination to the distal end of the rod tip 218 in the embodiment shown in FIG. 17B, the sheath 204 has a single outer layer 226. A window curved to avoid retroreflection is secured to the distal end of the single outer layer 226.

Referring to FIG. 18, a two piece disposable sheath/illuminator unit 230 is shown. The endoscope has a first unit 232 of the two piece disposable sheath/illumination unit 230, a mounting and cover unit 232, that is mounted to the handle 32 of the imaging unit 22. The mounting and cover unit 232 has a drape 52 that extends over the handle 32 of the imaging unit 22 and the illumination pigtail 88 when used. The drape 52 is retained on a disposable sleeve 234 to hold the drape 52 until positioned over the handle 32. The second unit 236 of the disposable sheath/illumination unit 230, a disposable sheath 236, contains the elongated tube that covers the probe 29. This second unit 236 has a mounting mechanism 238 to secure to the first unit 232. It is therefore possible to remove the disposable sheath, the second unit, 236 and replace it with a new one while keeping the drape 52 that is mounted to the mounting and cover unit 232 over the handle.

Figure 19:
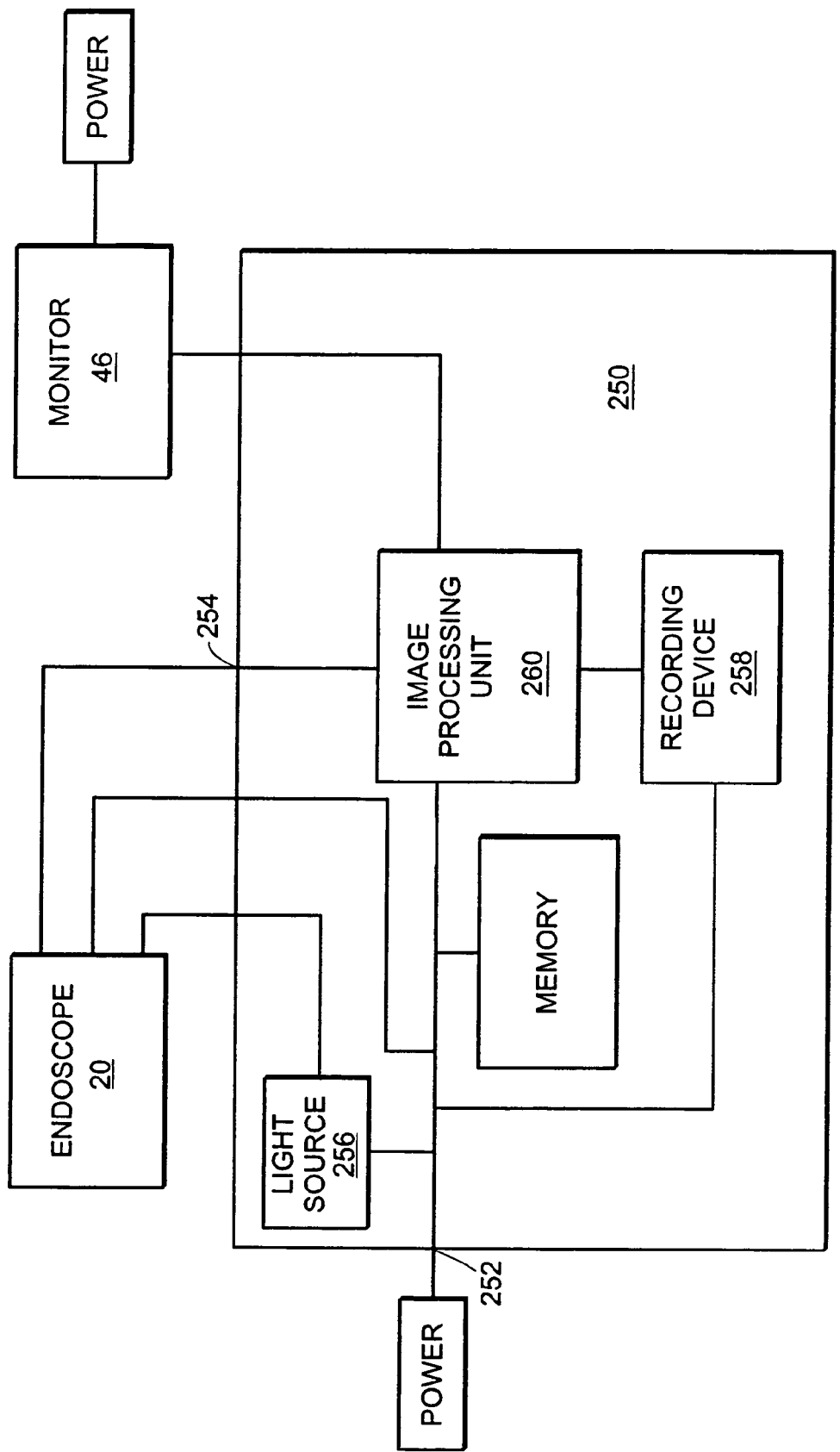
FIG. 19 is a schematic of a control unit for a preferred embodiment of the invention.

FIG. 19 is a schematic of a control unit 250 for the endoscope. This control unit 250 has a power source output 252, an input 254 for the image from the CCD and a light source 256. In addition to a processing unit 260 for processing the image data, the unit has a recording device 258 such as a CD writer to create a storable medium to retain data such as a baseline for the patient.

Figure 20:
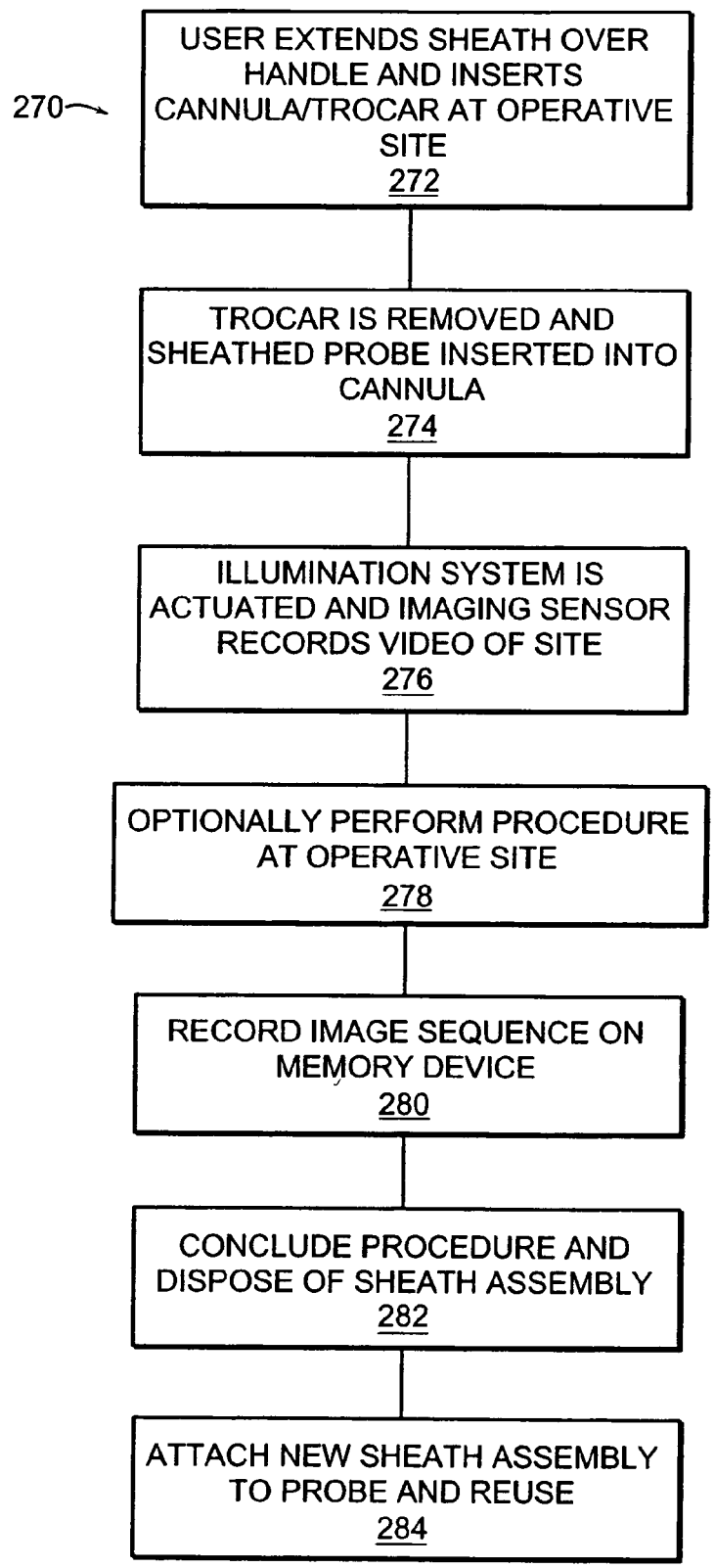
FIG. 20 illustrates a preferred method of using the invention.

The endoscope is used as shown generally in the process sequence 270 of FIG. 20. The patient comes to the user/physician's office. The physician or technician uses a double gloved technique where two sterilized gloves are placed on each of the physician's hands. The physician takes the handle/illuminator unit which is not sterilized in one hand and secure the sterilized sheath/illuminator unit with the other hand. The physician then takes the lighting cord and secure the light cord to the pigtail on the disposable sheath/illuminator unit. The power and image output are likewise connected to the control unit. With the endoscope connected to the control unit, the drape portion of the sheath assembly is extended 272 over the handle and down the cords to such a length to provide a sterile field. With this completed, the physician takes off the first pair of gloves and is ready to begin the procedure.

After medicating the site, the cannula with the trocar is inserted into the body by a standard technique of probing with the physician's hand. Once the cannula is in position, the trocar is removed 274 and the tip of the endoscope is placed into the cannula. The endoscope is secured to the cannula using a screw or other attachment mechanism. The system is actuated 276 and video recording is initiated so that the physician is able to move the cannula in and out and around to position the probe for viewing of the desired site or a monitor. The physician can perform a procedure 278 at the site using other instruments such as a laser scalpel or cautery tool, or electrosurgical tool and/or the operative channel in the probe or sheath assembly. The entire examination or operative procedure can be recorded 280 on a video disk or other memory device. The procedure is concluded and the sheath assembly can be disposed 282 of and another sterile sheath assembly can be attached 284 to the probe for another procedure.

The claims should not be read as limited to the described order or elements unless stated to that effect. Therefore, all embodiments that come within the scope and spirit of the following claims and equivalents thereto are claimed as the invention.

What is claimed is:

1. A method of imaging an orthopedic region within a patient comprising:
    connecting a removable sheath to a handle that is attached to a fiber optic imaging probe, the fiber optic imaging probe being adapted to transmit an image from a distal end to a proximal end through a plurality of imaging optical fibers positioned within an imaging tube, the fiber optic imaging probe having a lens system including a first lens element, a second lens element and an aperture stop positioned at the distal end of the imaging tube that couples light into the plurality of imaging optical fibers of the fiber optic imaging probe, the removable sheath being connected to the handle with a mounting mechanism such that the sheath extends over the distal end of the fiber optic imaging probe, the sheath having an outer diameter of less than 2 mm, a distal window and a plurality of illumination optical fibers extending between an inner tube and an outer tube of the removable sheath;
    inserting the sheath and the distal end of the probe through a cannula into the orthopedic region of the patient;
    illuminating the orthopedic region of the patient with light transmitted through the plurality of illumination optical fibers positioned around the fiber optic imaging probe; and
    detecting an image with an imaging device in the handle, the imaging device being optically coupled to the proximal end of the fiber optic imaging probe.

2. The method of claim 1 further comprising detecting the image with the lens system wherein the first lens element has a first convex surface facing a second convex surface of the second lens element.

3. The method of claim 1 further comprising coupling light at any position on a distal surface of the lens to a plurality of optical fibers in the probe such that the numerical aperture of light entering each fiber from a position varies as a function of angle.

4. The method of claim 1 further comprising coupling light through the fiber optic imaging probe with the lens system having a field of view that is matched to a numerical aperture of the plurality of imaging optical fibers.

5. The method of claim 1 further comprising coupling light through the probe, the probe having at least 10,000 imaging fibers within the imaging tube.

6. The method of claim 1 further comprising collecting light through the lens system that comprises an achromatic lens system.

7. The method of claim 1 wherein the step of connecting the removable sheath further comprises connecting the sheath such that light is collected by the probe through the lens system positioned within a lens tube at the distal end of the imaging tube.

8. The method of claim 7 further comprising connecting the disposable sheath such that a lens is positioned at a distal end of the sheath that couples light to the fiber optic imaging probe.

9. The method of claim 1 further comprising coupling light through the lens system comprising a non-telecentric lens system including the first lens element, the second lens element and the aperture stop.

10. The method of claim 1 wherein the step of connecting the removable sheath further comprises using the window at the distal end to seal the distal end of the probe with the sheath.

11. The method of claim 1 further comprising connecting the sheath including a tube for passing a tool to the distal end of the endoscope.

12. The method of claim 1 further comprising using a working channel in the probe or the sheath.

13. The method of claim 1 further comprising connecting the plurality of illumination fibers that fill an annular cavity between the inner tube and the outer tube to a light source with the handle, the handle including a charge coupled device and a plurality of lenses.

14. The method of claim 1 further comprising connecting the sheath that includes the annular illumination channel extending through the sheath that is coupled to a light source in a control unit with a connector.

15. The method of claim 1 further comprising connecting the imaging device to an image processor in a control unit.

16. The method of claim 1 further comprising using a connecting hub on the handle that connects to a mounting device on the sheath, the device having a sleeve providing a sterile barrier extending about the handle, the device being connectable to a cannula having a luer and a removable trocar.

17. The method of claim 1 further comprising inserting the cannula into a body to be examined, removing a trocar from the cannula prior to the step of inserting the sheath and probe into the cannula.

18. The method of claim 1 further comprising providing a fluid delivery port.

19. The method of claim 18 further comprising using the fluid port to rinse the orthopedic region with a fluid.

20. The method of claim 18 further comprising inserting a fluid through a port on the cannula.

21. The method of claim 18 further comprising inserting a medication through the fluid port.

22. The method of claim 1 further comprising removing the sheath from the handle and attaching a second removable sheath.

23. The method of claim 22 further comprising performing a second imaging procedure in an orthopedic region with the fiber optic imaging probe and the second removable sheath.

24. The method of claim 1 further comprising detaching the handle with the imaging device from the imaging probe.

25. The method of claim 24 further comprising using an imaging probe having a lens at a proximal end of an imaging probe housing.

26. The method of claim 1 further comprising using a lens holding tube that holds the first lens element, the second lens element and the aperture stop.

27. The method of claim 1 further comprising using the first lens element and the second lens element to provide a color corrected image.

28. A method of imaging an orthopedic region within a patient using an endoscope inserted through a cannula, the endoscope being attached to a removable sheath having a diameter of less than 2 mm for insertion through the cannula, the method comprising:
 connecting a removable sheath to a handle that is attached to a fiber optic imaging probe that transmits an image from a distal end to a proximal end through a plurality of imaging optical fibers positioned within an imaging tube, the fiber optic imaging probe having a lens system including a first lens element, a second lens element and an aperture stop positioned at the distal end of the fiber optic imaging probe that couples light into a plurality of imaging fibers of the fiber optic imaging probe, the removable sheath being connected to the handle with a mounting mechanism such that the sheath extends over the distal end of the fiber optic imaging probe, the removable sheath having an outer tube with a diameter of less than 2 mm, a distal window and a plurality of illumination optical fibers that are optically coupled to a light source with an optical fiber connector in the handle;
 inserting the sheath and the fiber optic imaging probe into the orthopedic region of the patient;
 illuminating the orthopedic region of the patient with light transmitted through the plurality of illumination optical fibers positioned within an annular cavity between the outer tube and an inner tube of the sheath, the plurality of optical fibers filling the annular cavity to provide an annular illumination channel around the fiber optic imaging probe;
 detecting an image with an imaging device in the handle, the imaging device being optically coupled to the proximal end of the fiber optic imaging probe;
 removing the sheath and probe from the patient; and
 removing the sheath from the fiber optic imaging probe.

29. The method of claim 28 further comprising detecting the image with the lens system wherein the first lens element has a first convex surface facing a second convex surface of the second lens element.

30. The method of claim 28 further comprising coupling light at any position on a distal surface of the lens to a plurality of optical fibers in the probe such that the numerical aperture of light entering each fiber from a position varies as a function of angle.

31. The method of claim 28 further comprising using the fiber optic imaging probe by collecting an image with the lens system having a field of view that is matched to a numerical aperture of the plurality of imaging optical fibers.

32. The method of claim 28 further comprising using a probe having at least 3000 imaging fibers.

33. The method of claim 28 further comprising collecting light with an achromatic lens system.

34. The method of claim 28 further comprising using a disposable sheath having the distal window that seals the imaging probe within the sheath.

35. The method of claim 34 further comprising collecting light through a lens at the distal end of the disposable sheath.

36. The method of claim 28 further comprising collecting light through the lens system, the lens system including a non-telecentric system including the first lens element, the second lens element and the aperture stop.

37. The method of claim 28 further comprising optically coupling a light source that is external to the handle to the plurality of illumination optical fibers with the handle.

38. The method of claim 28 further comprising passing a tool to the distal end of the endoscope through a tube in the removable sheath.

39. The method of claim 28 further comprising providing a working channel within the endoscope.

40. The method of claim 28 further comprising using a sheath having an illumination fiber optic system coupled to a light source through the handle, the handle including a charge coupled device and a plurality of lenses.

41. The method of claim 28 further comprising optically coupling the illumination fibers extending through the sheath to a light source.

42. The method of claim 28 further comprising connecting the imaging device to an image processor in a control unit.

43. The method of claim 28 further comprising using a connecting hub that connects to a mounting device on the sheath, the device having a sleeve providing a sterile barrier extending about the handle, the device being connectable to a cannula having a luer and a removable trocar.

44. The method of claim 28 further comprising inserting a cannula into a body to be examined, removing a trocar from the cannula and inserting the sheath and probe into the cannula.

45. A method of performing diagnostic orthopedic imaging of a patient comprising:
 connecting a removable sheath to a handle that is attached to a fiber optic imaging probe such that an image can be transmitted through a plurality of imaging fibers extending within an imaging tube from a distal end to a proximal end, the image being collected through an achromatic lens system including a first lens element, a second lens element and an aperture stop that are optically coupled to the plurality of imaging optical fibers in the probe, the removable sheath having an outer diameter of less than 2 mm and that is connected to the handle with a mounting mechanism, the removable sheath having a distal window to seal the distal end of the fiber optic imaging probe within the sheath;
 inserting the fiber optic imaging probe and the attached sheath through a cannula and into an orthopedic site of the patient;
 illuminating a portion of the orthopedic site with light directed through a plurality of illumination optical fibers extending within an annular cavity between an outer tube and inner tube of the sheath to provide an annular illumination channel within the sheath and around the imaging optical fibers; and
 detecting an image with an imaging device in the handle, the imaging device being optically coupled to the proximal end of the fiber optic probe.

46. The method of claim 45 further comprising coupling light to the lens, wherein the first lens element has a first convex surface facing a second convex surface of the second lens element.

47. The method of claim 45 further coupling light at any position on a distal surface of the lens system to a plurality of optical fibers in the probe such that the numerical aperture of light entering each fiber from a position varies as a function of angle.

48. The method of claim 45 further comprising using a fiber optic coupler that is connected to the plurality of illumination optical fibers.

49. The method of claim 45 further comprising using a probe having at least 3000 imaging fibers.

50. The method of claim 45 further comprising using the achromatic lens system that has a field of view matched with a numerical aperture of the imaging fibers.

51. The claim 45 further comprising connecting to a disposable sheath having a window at the distal end to a distal end of the handle, the window being attached to the inner tube.

52. The method of claim 51 further comprising collecting light through a lens at a distal end of the disposable sheath.

53. The method of claim 45 further comprising using a non-telecentric lens system including the first lens element, the second lens element and the aperture stop.

54. The method of claim 45 further comprising coupling a light source to the plurality of illumination optical fibers that fill a cavity between the outer tube and the inner tube of the removable sheath.

55. The method of claim 45 further comprising inserting a tool to the distal end of the endoscope through a tube in the sheath.

56. The method of claim 45 further comprising using a working channel.

57. The method of claim 45 further comprising coupling a light source to the illumination optical fibers, light source being connected through the handle, the handle including a charge coupled device and a plurality of lenses.

58. The method of claim 45 further comprising coupling the illumination optical fibers extending through the sheath to a light source in a control unit with a connector.

59. The method of claim 45 further comprising connecting the imaging device to an image processor in a control unit.

60. The method of claim 45 further comprising using a connecting hub that connects to a mounting device on the sheath, the mounting device having a sleeve providing a sterile barrier extending about the handle, the device being connectable to a cannula having a luer and a removable trocar.

61. The method of claim 45 further comprising inserting the cannula into a body to be examined, removing a trocar from the cannula and inserting the sheath and probe into the cannula.

62. The method of claim 45 further comprising connecting the handle to a light source and an image processing device.

* * * * *